United States Patent
Robinson et al.

(10) Patent No.: US 10,583,207 B2
(45) Date of Patent: *Mar. 10, 2020

(54) LIPID-ENCAPSULATED GAS MICROSPHERE COMPOSITIONS AND RELATED METHODS

(71) Applicant: Lantheus Medical Imaging, Inc., North Billerica, MA (US)

(72) Inventors: Simon P. Robinson, Stow, MA (US); Robert W. Siegler, Chelmsford, MA (US); David C. Onthank, Groton, MA (US); Nhung Tuyet Nguyen, Westford, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/203,725

(22) Filed: Jul. 6, 2016

(65) Prior Publication Data

US 2016/0331851 A1 Nov. 17, 2016

Related U.S. Application Data

(63) Continuation of application No. PCT/US2015/067615, filed on Dec. 28, 2015.

(60) Provisional application No. 62/098,453, filed on Dec. 31, 2014.

(51) Int. Cl.
| | | |
|---|---|---|
| *A61K 49/22* | (2006.01) | |
| *A61K 9/50* | (2006.01) | |
| *A61K 47/10* | (2017.01) | |
| *A61K 47/24* | (2006.01) | |

(52) U.S. Cl.
CPC .......... *A61K 49/223* (2013.01); *A61K 9/5089* (2013.01); *A61K 47/10* (2013.01); *A61K 47/24* (2013.01)

(58) Field of Classification Search
None
See application file for complete search history.

(56) References Cited

U.S. PATENT DOCUMENTS

| | | |
|---|---|---|
| 3,873,564 A | 3/1975 | Schneider et al. |
| 4,089,801 A | 5/1978 | Schneider |
| 4,224,179 A | 9/1980 | Schneider |
| 4,229,360 A | 10/1980 | Schneider et al. |
| 5,045,304 A | 9/1991 | Schneider et al. |
| 5,053,217 A | 10/1991 | Lehigh |
| 5,088,499 A | 2/1992 | Unger |
| 5,123,414 A | 6/1992 | Unger |
| 5,149,319 A | 9/1992 | Unger |
| 5,205,290 A | 4/1993 | Unger |
| 5,209,720 A | 5/1993 | Unger |
| 5,228,446 A | 7/1993 | Unger et al. |
| 5,230,882 A | 7/1993 | Unger |
| 5,271,928 A | 12/1993 | Schneider et al. |
| 5,281,408 A | 1/1994 | Unger |
| 5,305,757 A | 4/1994 | Unger et al. |
| 5,334,381 A | 8/1994 | Unger |
| 5,348,016 A | 9/1994 | Unger et al. |
| 5,352,435 A | 10/1994 | Unger |
| 5,358,702 A | 10/1994 | Unger |
| 5,368,840 A | 11/1994 | Unger |
| 5,380,519 A | 1/1995 | Schneider et al. |
| 5,393,524 A | 2/1995 | Quay |
| 5,409,688 A | 4/1995 | Quay |
| 5,413,774 A | 5/1995 | Schneider et al. |
| 5,445,813 A | 8/1995 | Schneider et al. |
| 5,456,900 A | 10/1995 | Unger |
| 5,456,901 A | 10/1995 | Unger |
| 5,469,854 A | 11/1995 | Unger et al. |
| 5,527,521 A | 6/1996 | Unger |
| 5,531,980 A | 7/1996 | Schneider et al. |
| 5,542,935 A | 8/1996 | Unger et al. |
| 5,547,656 A | 8/1996 | Unger |
| 5,558,092 A | 9/1996 | Unger et al. |
| 5,558,094 A | 9/1996 | Quay |
| 5,558,853 A | 9/1996 | Quay |
| 5,558,854 A | 9/1996 | Quay |
| 5,558,855 A | 9/1996 | Quay |
| 5,567,414 A | 10/1996 | Schneider et al. |
| 5,571,497 A | 11/1996 | Unger |
| 5,573,751 A | 11/1996 | Quay |
| 5,578,292 A | 11/1996 | Schneider et al. |
| 5,580,575 A | 12/1996 | Unger et al. |
| 5,585,112 A | 12/1996 | Unger et al. |
| 5,595,723 A | 1/1997 | Quay |
| 5,643,553 A | 7/1997 | Schneider et al. |

(Continued)

FOREIGN PATENT DOCUMENTS

| | | |
|---|---|---|
| CN | 101229382 A | 7/2008 |
| DE | 38 03 972 A1 | 8/1989 |

(Continued)

OTHER PUBLICATIONS

International Search Report and Written Opinion dated Aug. 12, 2016 for PCT/US2015/067615.
PCT/US2015/067615, Aug. 12, 2016, International Search Report and Written Opinion.
International Preliminary Report on Patentability dated Jul. 13, 2017 for PCT/US2015/067615.
[No Author Listed], U.S. Pharmacopeial Convention Herbal Medicines Compendium, USP-NF General Chapter <921> Water Determination. The United States Pharmacopeial Convention. Rockville, Maryland. Dec. 1, 2017;815-20.
[No Author Listed], http://www.acusphere.com/product/prod/_imagify.html. In existence as of Apr. 29, 2009. 1 page.

(Continued)

*Primary Examiner* — Jennifer Lamberski
(74) *Attorney, Agent, or Firm* — Wolf, Greenfield & Sacks, P.C.

(57) ABSTRACT

The invention provides, inter alia, improved lipid formulations used to generate lipid-encapsulated gas microspheres, and methods of their use.

22 Claims, 3 Drawing Sheets

(56) References Cited

U.S. PATENT DOCUMENTS

| | | |
|---|---|---|
| 5,656,211 A | 8/1997 | Unger et al. |
| 5,686,060 A | 11/1997 | Schneider et al. |
| 5,705,187 A | 1/1998 | Unger |
| 5,707,606 A | 1/1998 | Quay |
| 5,707,607 A | 1/1998 | Quay |
| 5,715,824 A | 2/1998 | Unger et al. |
| 5,733,572 A | 3/1998 | Unger et al. |
| 5,736,121 A | 4/1998 | Unger |
| 5,738,869 A | 4/1998 | Fischer et al. |
| 5,769,080 A | 6/1998 | Unger et al. |
| 5,770,222 A | 6/1998 | Unger et al. |
| 5,773,024 A | 6/1998 | Unger et al. |
| 5,776,429 A | 7/1998 | Unger et al. |
| 5,776,488 A | 7/1998 | Mori et al. |
| 5,830,430 A | 11/1998 | Unger et al. |
| 5,843,473 A | 12/1998 | Woodle et al. |
| 5,846,517 A | 12/1998 | Unger |
| 5,853,752 A | 12/1998 | Unger et al. |
| 5,853,755 A | 12/1998 | Foldvari |
| 5,874,062 A | 2/1999 | Unger |
| 5,897,851 A | 4/1999 | Quay et al. |
| 5,922,304 A | 7/1999 | Unger |
| 5,935,553 A | 8/1999 | Unger et al. |
| 5,985,246 A | 11/1999 | Unger |
| 5,997,898 A | 12/1999 | Unger |
| 6,001,335 A | 12/1999 | Unger |
| 6,028,066 A | 2/2000 | Unger |
| 6,033,645 A | 3/2000 | Unger et al. |
| 6,033,646 A | 3/2000 | Unger et al. |
| 6,039,557 A | 3/2000 | Unger et al. |
| 6,056,938 A | 5/2000 | Unger et al. |
| 6,066,331 A | 5/2000 | Barenholz et al. |
| 6,071,494 A | 6/2000 | Unger et al. |
| 6,071,495 A | 6/2000 | Unger et al. |
| 6,088,613 A | 7/2000 | Unger |
| 6,090,800 A | 7/2000 | Unger et al. |
| 6,117,414 A | 9/2000 | Unger |
| 6,120,794 A | 9/2000 | Liu et al. |
| 6,123,923 A | 9/2000 | Unger et al. |
| 6,139,819 A | 10/2000 | Unger et al. |
| 6,143,276 A | 11/2000 | Unger |
| 6,146,657 A | 11/2000 | Unger et al. |
| 6,214,375 B1 | 4/2001 | Modi |
| 6,231,834 B1 | 5/2001 | Unger et al. |
| 6,258,378 B1 | 7/2001 | Schneider et al. |
| 6,315,981 B1 | 11/2001 | Unger |
| 6,414,139 B1 | 7/2002 | Unger et al. |
| 6,416,740 B1 | 7/2002 | Unger |
| 6,443,898 B1 | 9/2002 | Unger et al. |
| 6,444,660 B1 | 9/2002 | Unger et al. |
| 6,461,586 B1 | 10/2002 | Unger |
| 6,479,034 B1 | 11/2002 | Unger et al. |
| 6,521,211 B1 | 2/2003 | Unger et al. |
| 6,528,039 B2 | 3/2003 | Unger |
| 6,537,246 B1 | 3/2003 | Unger et al. |
| 6,548,047 B1 | 4/2003 | Unger |
| 6,551,576 B1 | 4/2003 | Unger et al. |
| 6,572,840 B1 | 6/2003 | Toler |
| 6,576,220 B2 | 6/2003 | Unger |
| 6,716,412 B2 | 4/2004 | Unger |
| 6,773,696 B2 | 8/2004 | Unger |
| 6,884,407 B1 | 4/2005 | Unger |
| 6,943,692 B2 | 9/2005 | Castner et al. |
| 6,998,107 B2 | 2/2006 | Unger |
| 7,344,705 B2 | 3/2008 | Unger |
| 8,084,056 B2 | 12/2011 | Hui et al. |
| 8,658,205 B2 | 2/2014 | Hui et al. |
| 8,685,441 B2 | 4/2014 | Hui et al. |
| 8,747,892 B2 | 6/2014 | Hui et al. |
| 9,545,457 B2 | 1/2017 | Hui et al. |
| 9,789,210 B1 | 10/2017 | Robinson et al. |
| 9,913,919 B2 | 3/2018 | Robinson et al. |
| 10,022,460 B2 | 7/2018 | Robinson et al. |
| 10,220,104 B2 | 3/2019 | Robinson et al. |
| 2003/0044354 A1 | 3/2003 | Carpenter et al. |
| 2004/0057991 A1 | 3/2004 | Hui et al. |
| 2005/0163716 A1* | 7/2005 | Unger ............ A61K 9/127 424/9.52 |
| 2007/0071685 A1 | 3/2007 | Schneider et al. |
| 2008/0009561 A1 | 1/2008 | Unger et al. |
| 2008/0118435 A1 | 5/2008 | Unger |
| 2010/0089803 A1 | 4/2010 | Lavi et al. |
| 2012/0027688 A1 | 2/2012 | Hui et al. |
| 2012/0128595 A1* | 5/2012 | Hui ............ A61K 9/1277 424/9.5 |
| 2012/0263009 A1 | 10/2012 | Lim et al. |
| 2013/0022550 A1 | 1/2013 | Unger et al. |
| 2013/0123781 A1 | 5/2013 | Grubbs et al. |
| 2013/0309174 A1 | 11/2013 | Hui et al. |
| 2013/0309175 A1 | 11/2013 | Hui et al. |
| 2014/0328767 A1 | 11/2014 | Wang |
| 2016/0000943 A1 | 1/2016 | Unger et al. |
| 2016/0030596 A1 | 2/2016 | Kheir et al. |
| 2016/0331851 A1 | 11/2016 | Robinson et al. |
| 2017/0258946 A1 | 9/2017 | Robinson et al. |
| 2017/0312375 A1 | 11/2017 | Hui et al. |
| 2017/0319718 A1 | 11/2017 | Robinson et al. |
| 2017/0360966 A1 | 12/2017 | Robinson et al. |
| 2018/0008732 A1 | 1/2018 | Robinson et al. |
| 2018/0221516 A1 | 8/2018 | Robinson et al. |
| 2019/0142978 A1 | 5/2019 | Robinson et al. |
| 2019/0201559 A1 | 7/2019 | Robinson et al. |
| 2019/0255197 A1 | 8/2019 | Robinson et al. |

FOREIGN PATENT DOCUMENTS

| | | |
|---|---|---|
| EP | 0 052 575 A2 | 5/1982 |
| EP | 0 077 752 A2 | 4/1983 |
| EP | 0 224 934 A2 | 6/1987 |
| EP | 0 231 091 A1 | 8/1987 |
| EP | 0 274 961 A1 | 7/1988 |
| EP | 0 314 764 A1 | 5/1989 |
| EP | 0 324 938 A1 | 7/1989 |
| EP | 0 338 971 A1 | 10/1989 |
| EP | 0 349 429 A2 | 1/1990 |
| EP | 0 458 745 A1 | 11/1991 |
| EP | 0 554 213 A1 | 8/1993 |
| EP | 0 901 793 A1 | 3/1999 |
| EP | 0 957 942 A2 | 11/1999 |
| JP | 63-60943 | 3/1988 |
| JP | 63-277618 | 11/1988 |
| JP | 2-149336 A | 6/1990 |
| JP | 8-151335 A | 6/1996 |
| WO | WO 80/02365 A1 | 11/1980 |
| WO | WO 82/01642 A1 | 5/1982 |
| WO | WO 85/02772 A1 | 7/1985 |
| WO | WO 89/10118 A1 | 11/1989 |
| WO | WO 90/04384 A1 | 5/1990 |
| WO | WO 90/14846 A1 | 12/1990 |
| WO | WO 91/00086 A1 | 1/1991 |
| WO | WO 91/09629 A1 | 7/1991 |
| WO | WO 91/15244 A2 | 10/1991 |
| WO | WO 91/15753 A1 | 10/1991 |
| WO | WO 92/10166 A1 | 6/1992 |
| WO | WO 92/15284 A1 | 9/1992 |
| WO | WO 92/17212 A1 | 10/1992 |
| WO | WO 92/17514 A1 | 10/1992 |
| WO | WO 92/22247 A1 | 12/1992 |
| WO | WO 92/22249 A1 | 12/1992 |
| WO | WO 92/22298 A1 | 12/1992 |
| WO | WO 93/05819 A1 | 4/1993 |
| WO | WO 93/06869 A1 | 4/1993 |
| WO | WO 93/13802 A1 | 7/1993 |
| WO | WO 94/09829 A1 | 5/1994 |
| WO | WO 94/16739 A1 | 8/1994 |
| WO | WO 94/21301 A1 | 9/1994 |
| WO | WO 94/21302 A1 | 9/1994 |
| WO | WO 94/28780 A2 | 12/1994 |
| WO | WO 94/28797 A1 | 12/1994 |
| WO | WO 94/28873 A1 | 12/1994 |
| WO | WO 94/28874 A1 | 12/1994 |
| WO | WO 95/03835 A1 | 2/1995 |
| WO | WO 95/06518 A1 | 3/1995 |
| WO | WO 95/07072 A2 | 3/1995 |

(56) References Cited

FOREIGN PATENT DOCUMENTS

| | | |
|---|---|---|
| WO | WO 95/12387 A1 | 5/1995 |
| WO | WO 95/15118 A1 | 6/1995 |
| WO | WO 95/16467 A1 | 6/1995 |
| WO | WO 95/23615 A1 | 9/1995 |
| WO | WO 95/24184 A1 | 9/1995 |
| WO | WO 95/26205 A1 | 10/1995 |
| WO | WO 95/32005 A1 | 11/1995 |
| WO | WO 95/32006 A1 | 11/1995 |
| WO | WO 96/04018 A1 | 2/1996 |
| WO | WO 96/08234 A1 | 3/1996 |
| WO | WO 96/09793 A1 | 4/1996 |
| WO | WO 96/31196 A1 | 10/1996 |
| WO | WO 96/40281 A2 | 12/1996 |
| WO | WO 96/40285 A1 | 12/1996 |
| WO | WO 97/00638 A2 | 1/1997 |
| WO | WO 97/40679 A1 | 11/1997 |
| WO | WO 97/40858 A1 | 11/1997 |
| WO | WO 97/48337 A1 | 12/1997 |
| WO | WO 98/04292 A2 | 2/1998 |
| WO | WO 98/10798 A1 | 3/1998 |
| WO | WO 98/10799 A1 | 3/1998 |
| WO | WO 98/17324 A2 | 4/1998 |
| WO | WO 98/18495 A2 | 5/1998 |
| WO | WO 98/18498 A2 | 5/1998 |
| WO | WO 98/18500 A2 | 5/1998 |
| WO | WO 98/18501 A2 | 5/1998 |
| WO | WO 98/42384 A1 | 10/1998 |
| WO | WO 98/51284 A1 | 11/1998 |
| WO | WO 99/08714 A1 | 2/1999 |
| WO | WO 99/13919 A1 | 3/1999 |
| WO | WO 99/30620 A1 | 6/1999 |
| WO | WO 99/36104 A2 | 7/1999 |
| WO | WO 99/39738 A1 | 8/1999 |
| WO | WO 00/45856 A2 | 8/2000 |
| WO | WO 2004/030617 A1 | 4/2004 |
| WO | WO 2013/013067 A2 | 1/2013 |

OTHER PUBLICATIONS

Chapman, Physicochemical properties of Phospholipids and Lipid-Water Systems. Liposome Technology: Preparation of Liposomes—Chapter 1. Gregory Gregoriadis, Ed. CRC Press, Boca Raton, FL. 1984;1:1-18.
Deamer, Preparation of Solvent Vaporization Liposomes. Liposome Technology: Preparation of Liposomes—Chapter 3. Gregory Gregoriadis, Ed. CRC Press, Boca Raton, FL. 1984;1:29-35.
Lelkes, The Use of French Pressed Vesicles for Efficient Incorporation of Bioactive Macromolecules and as Drug Carriers In Vitro and In Vivo. Liposome Technology: Preparation of Liposomes—Chapter 5. Gregory Gregoriadis, Ed. CRC Press, Boca Raton, FL. 1984;1:51-65.
Weder et al., The Preparation of Variably Sized Homogeneous Liposomes for Laboratory, Clinical, and Industrial Use by Controlled Detergent Dialysis. Liposome Technology: Preparation of Liposomes—Chapter 7. Gregory Gregoriadis, Ed. CRC Press, Boca Raton, FL. 1984;1:279-107.
[No Author Listed] Division of new drug chemistry document relating to Definity. Review date, Feb. 15, 2001.
[No Author Listed] EMEA Scientific discussion relating to Sonovue. Updated until Oct. 1, 2004. 1 page.
[No Author Listed] Definity FDA Approval Label. Initial US Approval: 2001. U.S. Food and Drug Administration. Silver Spring, Maryland. Revised Aug. 2015 19 pages.
Bedu-Addo, F.K., et al., "Effects of polyethyleneglycol chain length and phospholipids acyl chain composition on the interaction of polyethyleneglycol-phospholipid conjugants with phospholipids: implications in liposomal drug delivery," Pharm. Res., May 1996, 13(5), 710-717.
Belsito, S., et al., "Sterically stabilized liposomes of DPPC/DPPE-PEG 2000—A spin label ESR & spectrophotometric study," Biophysical Chem., May 10, 1998, 75(1), 33-43.
Blomley et al., "Microbubble contrast agents: a new era in ultrasound"; Clinical Review XP008001399, BMJ, vol. 322, pp. 1222-1225 (May 19, 2001).
De Jong et al., New ultrasound contrast agents and technological innovations. Ultrasonics. Jun. 1996;34(2-5):587-90.
Feinstein et al., "Two-Dimensional Contrast Echocardiography. I. In Vitro Development and Quantitative Analysis of Echo Contrast Agents", JACC, vol. 3, No. 1, pp. 14-20 (1984).
Fritzsch et al., "Preclinical and Clinical Results with an Ultrasonic Contrast Agent", Inv. Rad., vol. 23, pp. S302-S305, Sep. 1988.
Gabizon et al., "Liposome formulations with prolonged circulation time in blood and enhanced uptake by tumors", Proc. Natl. Acad. Sci., vol. 85, pp. 6949-6953 (1988).
Goldberg, et al., "Ultrasound contrast agents: a review," Ultrasound in Med. & Biol., 1994, 20(4), 319-333.
Gregodiadis, G., et al. (Eds.), "Liposome technology: preparation of liposomes," and Deamer: "Preparation of solvent vaporization liposomes," CRC Press, Inc., 1984, CRC Press, Inc., XP002101586, vol. 1, 30-35, 51-65, 79-107.
Gross, U. et al., "Phosholipid vesiculated fluorocarbons promising trend in blood substitutes" Biomat., Art. Cells & Immob. Biotech., 1992, vol. 20, (2-4) pp. 831-833.
Hettiarachchi et al., On-chip generation of microbubbles as a practical technology for manufacturing contrast agents for ultrasonic imaging. Lab Chip. Apr. 2007;7(4):463-8. Epub Mar. 8, 2007.
Hope et al., "Generation of Multilamellar and Unilamellar Phospholipid Vesicles", Chemistry and Physics of Lipids, vol. 40, pp. 89-107 (1986).
Ishida et al., Accelerated clearance of PEGylated liposomes in rats after repeated injections. J Control Release. Feb. 14, 2003;88(1):35-42.
Kitzman et al., Efficacy and safety of the novel ultrasound contrast agent perflutren (DEFINITY) in patients with suboptimal baseline left ventricular echocardiographic images. Am J Cardiol. Sep. 15, 2000;86(6):669-74.
Nikolova, A., et al., "Effect of grafted PEG-2000 on the size and permeability of vesicles," Biochim Biophys Acta, Nov. 22, 1996, 1304(2), 120-128.
Ohki, et al., "Short & long range calcium-induced lateral phase separations in ternary mixtures of phosphatidic acid phosphatidylcholine and phosphatidylethanolamine," Chem. & Physics of Lipids, 1989, 50(2), 109-118.
Ophir et al., "Contrast Agents in Diagnostic Ultrasound", Ultrasound in Med. & Biol., vol. 15, No. 4, pp. 319-333 (1989).
Sarkar et al., Growth and dissolution of an encapsulated contrast microbubble: effects of encapsulation permeability. Ultrasound Med Biol. Aug. 2009;35(8):1385-96. doi: 10.1016/j.ultrasmedbio.2009.04.010.
Schutt et al., "Osmotically Stabilized Microbubble Sonographic Contrast Agents", Acad. Radiol., vol. 3, Suppl. 2, pp. S188-S190 (Aug. 1996).
Senior et al., Investigators. Detection of coronary artery disease with perfusion stress echocardiography using a novel ultrasound imaging agent: two Phase 3 international trials in comparison with radionuclide perfusion imaging. Eur J Echocardiogr. Jan. 2009;10(1):26-35.
Senior, Imagify (perflubutane polymer microspheres) injectable suspension for the assessment of coronary artery disease. Expert Rev Cardiovasc Ther. May 2007;5(3):413-21.
Swanson et al., "Enhancement Agents for Ultrasound: Fundamentals", Pharmaceuticals in Medical Imaging, Chapter 22, pp. 682-687 (1990).
Szoka, et al., "Comparative properties and methods of preparation of liqid vesicles (Liposomes)," Ann. Rev. Biophys. Bioeng., 1980,9, 467-508.
Unger et al., "Gas filled lipid bilayers as imaging contrast agents," J. Liposome Res., 1994, 4(2), 861-874.
Unger et al., "Gas-filled lipid bilayers as ultrasound contrast agent," Invest. Radiol., 1994, 29S2, S134-S136.
Unger et al., "In Vitro Studies of a New Thrombus-Specific Ultrasound Contrast Agent", American Journal of Cardiology, vol. 81,

(56) References Cited

OTHER PUBLICATIONS

No. 12, Suppl. A, pp. 58G-61G, XP-002087505, Jun. 12, 1998 and Symposium: Ninth International Congress on Echocardiography: Clinical Cardiology, 1997.
Unger et al., "Liposomal MR Contrast Agents", J. Liposome Research, 4(2), pp. 811-834 (1994).
Unger et al., "Hepatic Metastases: Liposomal Gd-DTPA-enhanced MR Imaging", Radiology, vol. 171, No. 1, pp. 81-85 (1989).
Wang et al., Anti-PEG IgM elicited by injection of liposomes is involved in the enhanced blood clearance of a subsequent dose of PEGylated liposomes. J Control Release. Jun. 4, 2007;119(2):236-44. Epub Feb. 24, 2007.
Yuda et al., Prolongation of liposome circulation time by various derivatives of polyethyleneglycols. Biol Pharm Bull. Oct. 1996;19(10):1347-51.
Extended European Search Report for EP App. No. 15876086.8 dated Jul. 23, 2018.
[No Author Listed], Liposome Drug Products—Chemistry, Manufacturing, and Controls; Human Pharmacokinetics and Bioavailability; and Labeling Documentation—Guidance for Industry—Draft Guidance. U.S. Department of Health and Human Services, Food and Drug Administration, Center for Drug Evaluation and Research. Silver Spring, MD. Oct. 2015 17 pages.
Fritz et al., Phase I clinical trials of MRX-115. A new ultrasound contrast agent. Invest Radiol. Dec. 1997;32(12):735-40.
Fritz et al., Preclinical Studies of MRX-115: Safety Evaluations of a Myocardial Perfusion Agent. Acad. Radiol. Aug. 1996;3(Suppl 2):S185-7.
Klibanov, Preparation of targeted microbubbles: ultrasound contrast agents for molecular imaging. Med. Biol. Eng. Comput. 2009;47:875-82.
Metzger-Rose et al., Ultrasonographic Detection of Testicular Ischemia in a Canine Model Using Phospholipid Coated Microbubbles (MRX-115). J. Ultrasound Med. 1997;16:317-24.
Unger et al., Gas-Filled Liposomes as Echocardiographic Contrast Agents in Rabbits with Myocardial Infarcts. Investigative Radiology. Dec. 1993;28(12):1155-9.
Unger et al., Nitrogen-filled Liposomes as a Vascular US Contrast Agent: Preliminary Evaluation. Radiology. Nov. 1992 ;185:453-6.
Unger et al., Therapeutic applications of lipid-coated microbubbles. Advanced Drug Delivery Reviews. 2004;56:1291-1314.

\* cited by examiner

FIG. 1. Stability of LB/PG* formulation versus DEFINITY®
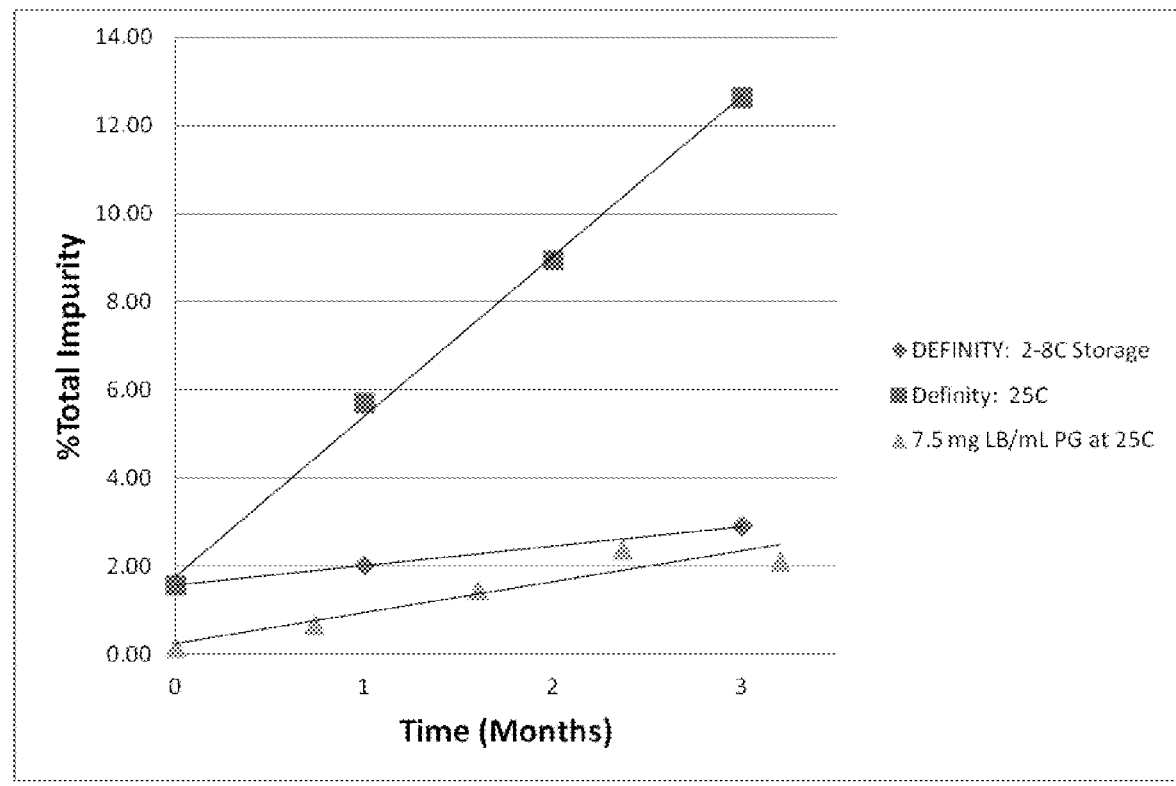
*177 mg of PG containing LB (0.72 wt% LB; ratio of 1:138 for LB:PG).

FIG. 2.  Stability of 3.75 mg LB/mL PG/G formulation* versus DEFINITY®
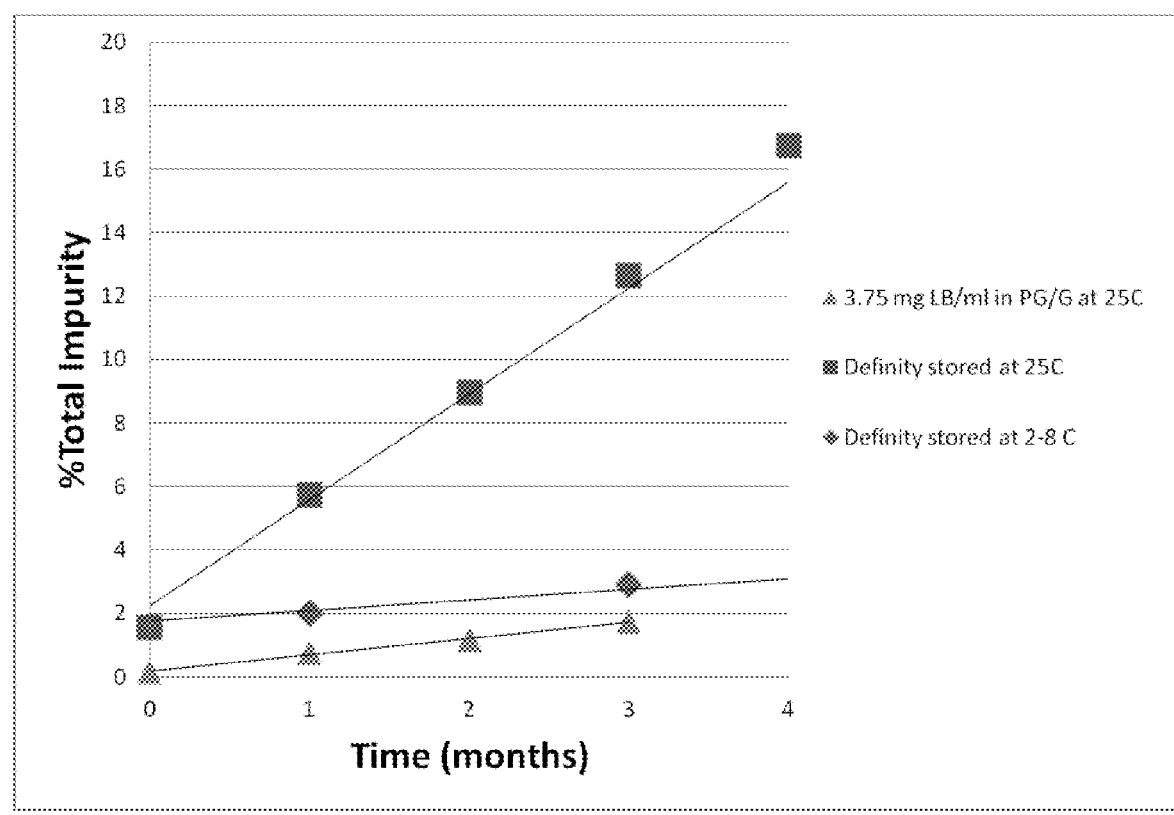
*391 mg of PG/G containing LB (0.33 wt% LB:44.9 wt% PG:54.8 wt% G; ratio of 1:138:168 for LB:PG:G).

FIG. 3. Stability of 3.75 mg Lipid Blend/mL Buffered PG/G formulation* versus DEFINITY®:
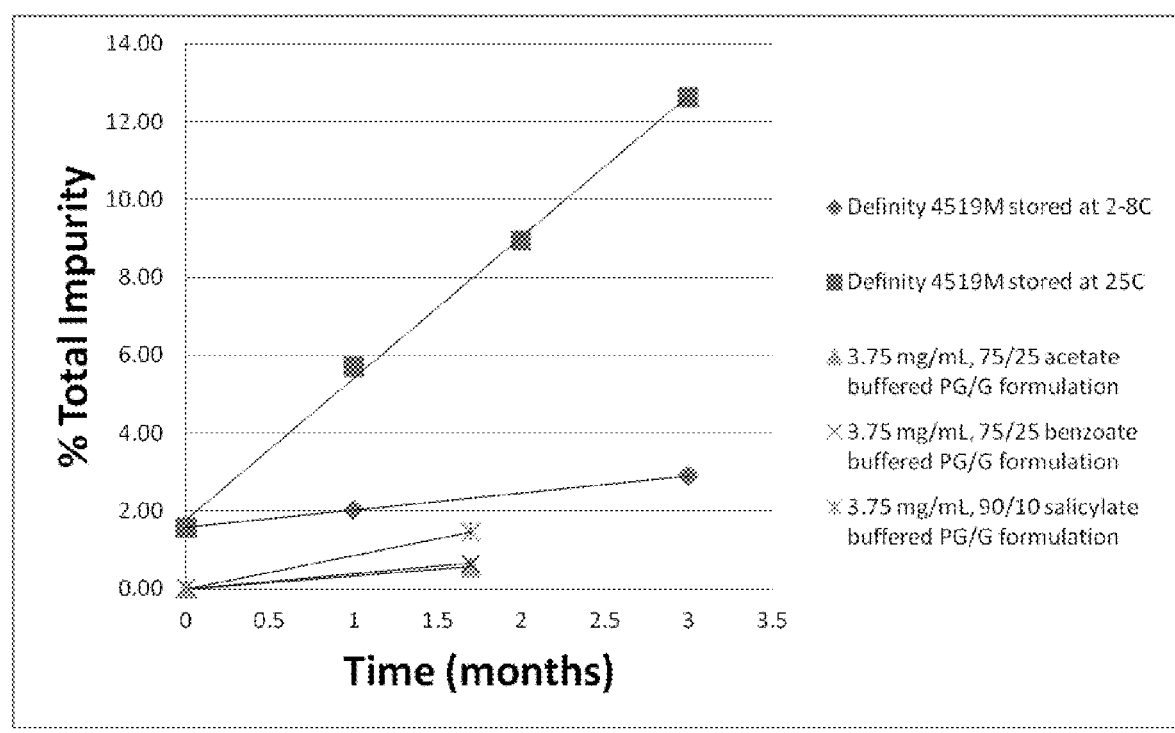
* 5mM buffer in 391 mg of PG/G containing LB, (0.33 wt% LB; 44.9 wt% PG; 54.8 wt% G; ratio of 1:138:168 for LB:PG:G). Ratios represent sodium acetate to acetic acid, sodium benzoate to benzoic acid, sodium salicylate to salicylic acid.

LIPID-ENCAPSULATED GAS MICROSPHERE COMPOSITIONS AND RELATED METHODS

RELATED APPLICATIONS

This application is a continuation of and claims the benefit under 35 U.S.C. § 120 and § 365(c) of International Application No. PCT/US2015/067615, with an international filing date of Dec. 28, 2015, which claims the benefit under 35 U.S.C. § 119(e) of U.S. provisional application Ser. No. 62/098,453, filed Dec. 31, 2014, both of which are incorporated by reference herein in their entirety.

SUMMARY

The invention provides, in part, new and improved formulations for making ultrasound contrast agents as well as preparations of ultrasound contrast agents themselves. Such formulations are less complex in their composition, their method of manufacture and their method of use and, surprisingly, more robust than prior art formulations used to make ultrasound contrast agents, including more stable at room temperature for extended periods of time. Such formulations can be used to make ultrasound contrast agents, surprisingly, without complex manipulation.

Provided herein are these new formulations, kits comprising these new formulations, methods of using these formulations including methods of using these formulations to make ultrasound contrast agents, and compositions or preparations of the lipid-encapsulated gas microspheres themselves. These new formulations include the non-aqueous mixtures described in greater detail herein.

In one aspect, provided herein is a composition consisting of or consisting essentially of a non-aqueous mixture of DPPA, DPPC and PEG5000-DPPE in propylene glycol and glycerol and a buffer.

In another aspect, provided herein is a composition consisting of or consisting essentially of a non-aqueous mixture of DPPA, DPPC and PEG5000-DPPE in propylene glycol and a buffer.

In another aspect, provided herein is a composition consisting of or consisting essentially of a non-aqueous mixture of DPPA, DPPC and PEG5000-DPPE in glycerol and a buffer.

The buffer may be, without limitation, an acetate buffer (e.g., a combination of sodium acetate and acetic acid), or a benzoate buffer (e.g., a combination of sodium benzoate and benzoic acid), or a salicylate buffer (e.g., a combination of sodium salicylate and salicylic acid).

The foregoing compositions may be provided in a sterile container, optionally with a perfluorocarbon gas, and further optionally with instructions for use including instructions for activating such compositions in the presence of a perfluorocarbon gas and optionally in the presence of an aqueous diluent in order to generate lipid-encapsulated gas microspheres. The composition to be activated may comprise the aqueous diluent as a second phase and thus may be non-homogeneous prior to activation.

In another aspect, provided herein is a composition comprising a non-aqueous mixture of DPPA, DPPC and PEG5000-DPPE in propylene glycol and glycerol, and a perfluorocarbon gas.

In some embodiments, the weight to weight to weight (w/w/w) ratio of DPPA, DPPC and PEG5000-DPPE (combined) to propylene glycol to glycerol is in a range of about 1:50:50 to about 1:1000:1000, or about 1:100:100 to about 1:600:700. In some embodiments, the w/w/w ratio of DPPA, DPPC and PEG5000-DPPE (combined) to propylene glycol to glycerol is about 1:120:120 to about 1:400:400, or about 1:120:120 to about 1:300:300, or about 1:120:120 to about 1:250:250. In some embodiments, the w/w/w ratio of DPPA, DPPC and PEG5000-DPPE (combined) to propylene glycol to glycerol is about 1:100:150 to about 1:150:200. In some embodiments, the w/w/w ratio of DPPA, DPPC and PEG5000-DPPE (combined) to propylene glycol to glycerol is about 1:250:300 to about 1:300:350. In some embodiments, the w/w/w ratio of DPPA, DPPC and PEG5000-DPPE (combined) to propylene glycol to glycerol is about 1:500:600 to about 1:600:700. In some embodiments, the w/w/w ratio of DPPA, DPPC and PEG5000-DPPE (combined) to propylene glycol to glycerol is about 1:138:168 or about 1:276:336 or about 1:552:673.

In some embodiments, the w/w/w ratio of DPPA, DPPC and PEG5000-DPPE (combined) to propylene glycol to glycerol is about 0.75 mg: 103.5 mg: 126.2 mg. In some embodiments, the w/w/w ratio of DPPA, DPPC and PEG5000-DPPE (combined) to propylene glycol to glycerol is about 0.375 mg: 103.5 mg: 126.2 mg. In some embodiments, the w/w/w ratio of DPPA, DPPC and PEG5000-DPPE (combined) to propylene glycol to glycerol is about 0.1875 mg: 103.5 mg: 126.2 mg.

In another aspect, provided herein is a composition comprising a non-aqueous mixture of DPPA, DPPC and PEG5000-DPPE in propylene glycol, and a perfluorocarbon gas.

In some embodiments, the w/w ratio of DPPA, DPPC and PEG5000-DPPE (combined) to propylene glycol is in a range of about 1:10 to about 1:2000, or about 1:10 to about 1:1500, or about 1:10 to about 1:1000, or about 1:20 to about 1:2000, or about 1:50 to about 1:1000, or about 1:50 to about 1:600, or about 1:100 to about 1:600.

In some embodiments, the w/w ratio of DPPA, DPPC and PEG5000-DPPE (combined) to propylene glycol is about 1:100 to about 1:200, or about 1:100 to about 1:150. In some embodiments, the w/w ratio of DPPA, DPPC and PEG5000-DPPE (combined) to propylene glycol is about 1:200 to about 1:350, or about 1:250 to about 1:300. In some embodiments, the w/w ratio of DPPA, DPPC and PEG5000-DPPE (combined) to propylene glycol is about 1:500 to about 1:600, or about 1:525 to about 1:575. In some embodiments, the w/w ratio of DPPA, DPPC and PEG5000-DPPE (combined) to propylene glycol is about 1:138 or about 1:276 or about 1:552.

In some embodiments, the w/w ratio of DPPA, DPPC and PEG5000-DPPE (combined) to propylene glycol is about 0.75 mg: 103.5 mg or about 0.375 mg: 103.5 mg or about 0.1875 mg: 103.5 mg.

In another aspect, provided herein is a composition comprising a non-aqueous mixture of DPPA, DPPC and PEG5000-DPPE in glycerol, and a perfluorocarbon gas.

In some embodiments, the w/w ratio of DPPA, DPPC and PEG5000-DPPE (combined) to glycerol is in a range of about 1:10 to about 1:2000, or about 1:15 to about 1:1500, or about 1:50 to about 1:1000, or about 1:50 to about 1:7000, or about 1:100 to about 1:700. In some embodiments, the w/w ratio of DPPA, DPPC and PEG5000-DPPE (combined) to glycerol is about 1:100 to about 1:200 or about 1:125 to about 1:175. In some embodiments, the w/w ratio of DPPA, DPPC and PEG5000-DPPE (combined) to glycerol is about 1:250 to about 1:400, or about 1:300 to about 1:350. In some embodiments, the w/w ratio of DPPA, DPPC and PEG5000-DPPE (combined) to glycerol is about 1:550 to about 1:700 or about 1:650 to about 1:700. In some embodiments, the w/w ratio of DPPA, DPPC and PEG5000-DPPE (combined) to glycerol is about 1:168 or about 1:336 or about 1:673.

In some embodiments, the w/w ratio of DPPA, DPPC and PEG5000-DPPE (combined) to glycerol is about 0.75 mg: 126.2 mg, or about 0.375 mg: 126.2 mg, or about 0.1875 mg: 126.2 mg.

In other aspects, provided herein is a container comprising any of the foregoing compositions.

In some embodiments, the container is a single chamber container.

In some embodiments, the container comprises a first and a second chamber, and wherein the non-aqueous mixture is in the first chamber and the perfluorocarbon gas is in the second chamber.

In other aspects, provided herein is a container comprising any of the foregoing compositions in a first chamber and an aqueous diluent in a second chamber.

In other aspects, provided herein is a container comprising any of the foregoing compositions and an aqueous diluent, wherein the non-aqueous mixture is provided in a first chamber, the perfluorocarbon gas is provided in a second chamber, and the aqueous diluent is provided in a third chamber.

In some embodiments, the aqueous diluent is an aqueous saline solution. In some embodiments, the aqueous diluent is an aqueous buffered solution. In some embodiments, the aqueous diluent is an aqueous buffered saline solution.

In another aspect, provided herein is a composition comprising a mixture of DPPA, DPPC and PEG5000-DPPE in solid form, and a perfluorocarbon gas. The mixture of DPPA, DPPC and PEG5000-DPPE in solid form may be a blended solid form (e.g., a relatively homogeneous mixture of the lipids) or it may be a combination of the solid forms of each lipid (e.g., which may or may not be a homogeneous mixture of the lipids). In another aspect, provided herein is a container comprising the foregoing solid form composition. In some embodiments, the container is a container having a single chamber. In some embodiments, the container is a container having two chambers, wherein a first chamber comprises DPPA, DPPC and PEG5000-DPPE in solid form, and a second chamber comprises the perfluorocarbon gas. In some embodiments, the container is a container having two chambers, wherein a first chamber comprises DPPA, DPPC and PEG5000-DPPE in solid form and the perfluorocarbon gas, and a second chamber comprises (a) propylene glycol, (b) propylene glycol and glycerol, or (c) glycerol. The w/w/w ratios of the lipids combined to propylene glycol and/or to glycerol may be as stated above. In some embodiments, the container is a container having three chambers, wherein a first chamber comprises DPPA, DPPC and PEG5000-DPPE in solid form, a second chamber comprises the perfluorocarbon gas, and a third chamber comprises (a) propylene glycol, (b) propylene glycol and glycerol, or (c) glycerol. In some embodiments, the container is a container having an additional chamber comprising an aqueous diluent.

In another aspect, provided herein is a composition comprising lipid-encapsulated gas microspheres comprising DPPA, DPPC and PEG5000-DPPE and perfluorocarbon gas, in a non-aqueous solution comprising propylene glycol and glycerol.

In another aspect, provided herein is a composition comprising lipid-encapsulated gas microspheres comprising DPPA, DPPC and PEG5000-DPPE, in a non-aqueous solution comprising propylene glycol.

In another aspect, provided herein is a composition comprising lipid-encapsulated gas microspheres comprising DPPA, DPPC and PEG5000-DPPE and perfluorocarbon gas, in a non-aqueous solution comprising glycerol.

In some embodiments, the lipid-encapsulated gas microspheres have an average diameter ranging from about 1.0 microns to about 2.0 microns. In some embodiments, the lipid-encapsulated gas microspheres have an average diameter ranging from about 1.2 microns to about 2.0 microns. In some embodiments, the lipid-encapsulated gas microspheres have an average diameter of about 1.4 to 1.8 microns.

In some embodiments, the lipid-encapsulated gas microspheres are present in the composition at a concentration of greater than $10^8$/mL.

Various embodiments apply equally to the foregoing compositions and will be recited now.

In some embodiments, the non-aqueous mixture comprises less than 5% of water by weight (i.e., weight of water to weight of the combination of lipid and propylene glycol and/or glycerol). In some embodiments, the non-aqueous mixture comprises 1-4% water by weight. In some embodiments, the non-aqueous mixture comprises less than 1% water by weight.

In some embodiments, the composition is salt-free, meaning that it may comprise the counter-ions to the lipids in the composition but is free of other ions. The lipid counter-ions are typically cations such as sodium. Thus, in some embodiments the composition does not comprise anions. In some embodiments, the composition is free of sodium chloride. In some embodiments, the composition is free of chloride ions.

In some embodiments, the composition further comprises a buffer. In some embodiments, the composition further comprises a non-phosphate buffer. In some embodiments, the composition further comprises an acetate buffer, or a benzoate buffer, or a salicylate buffer.

In some embodiments, DPPA, DPPC and PEG5000-DPPE combined are present in a concentration of about 0.9 to about 8 mg lipid per ml of non-aqueous mixture, about 0.9 mg to about 7.5 mg lipid per ml non-aqueous mixture, about 2 mg to about 7.5 mg lipid per ml non-aqueous mixture, or about 2 mg to about 4 mg lipid per ml non-aqueous mixture. In some embodiments, DPPA, DPPC and PEG5000-DPPE combined are present in a concentration of about 0.94 mg to about 7.5 mg lipid per ml of non-aqueous mixture, or about 1.875 mg to about 7.5 mg lipid per ml of non-aqueous mixture, including about 1.875 mg to about 3.75 mg lipid per ml of non-aqueous mixture, and about 3.75 to about 7.5 mg lipid per ml of non-aqueous mixture. In some embodiments, DPPA. DPPC and PEG5000-DPPE are present in a ratio of about 10:82:8 (mole %).

In some embodiments, the non-aqueous mixture, alone or in combination with a perfluorocarbon gas, comprises less than 5% impurities when stored at room temperature for about 3 months. In some embodiments, the non-aqueous mixture, alone or in combination with a perfluorocarbon gas, comprises fewer impurities than DEFINITY® when both are stored at room temperature (i.e., when the composition and DEFINITY® are stored at room temperature).

In some embodiments, the perfluorocarbon gas is perfluoropropane gas.

In some embodiments, PEG5000-DPPE is MPEG5000-DPPE.

In some embodiments, the composition is provided in a vial. In some embodiments, the composition is provided in a vial with an actual volume of less than or equal to about 3.8 ml.

In some embodiments, the composition is provided in a vial with a V-bottom. In some embodiments, the composition is provided in a vial with a flat-bottom. In some embodiments, the composition is provided in a vial with a rounded-bottom. In some embodiments, the vial is a glass vial. In some embodiments, a composition comprising a non-aqueous mixture of DPPA, DPPC and PEG5000-DPPE combined in propylene glycol and glycerol, and a perfluorocarbon gas, is provided in a 2 ml Nipro (Wheaton) vial at a lipid concentration of about 3.75 mg/ml. In some embodiments, a composition comprising a non-aqueous mixture of DPPA, DPPC and PEG5000-DPPE combined in propylene glycol and glycerol, and a perfluorocarbon gas, is provided in a 2 ml Schott vial at a lipid concentration of about 3.75 mg/ml.

In some embodiments, the composition is provided in a single chamber container. In some embodiments, the composition is provided in a multiple chamber container. In some embodiments, the composition is provided in a first chamber and an aqueous diluent is provided in a second chamber. The aqueous diluent may be a saline solution or it may be saline-free. The aqueous diluent may be buffered solution or it may be buffer-free. The aqueous diluent may be a buffered saline solution.

In another aspect, provided herein is a kit comprising any of the foregoing compositions in a container. In some embodiments, the container is a single chamber container.

In some embodiments, the kit comprises a second container. In some embodiments, the second container comprises an aqueous diluent. In some embodiments, the second container is a pre-filled syringe.

In some embodiments, the container is a multi-chamber container. In some embodiments, the first container comprises the lipids (i.e., DPPA, DPPC and PEG5000-DPPE) in solid form, and the second container comprises propylene glycol or glycerol or propylene glycol and glycerol. A third container may comprise an aqueous diluent.

In some embodiments, the first container comprises the lipids in propylene glycol, and the second container comprises glycerol or aqueous diluent. Alternatively, the second container comprises glycerol and a third container comprises aqueous diluent.

In some embodiments, the first container comprises the lipids in glycerol, and the second container comprises propylene glycol or aqueous diluent. Alternatively, the second container comprises propylene glycol and a third container comprises aqueous diluent.

In some embodiments, the first container comprises the lipids in propylene glycol and glycerol, and the second container comprises aqueous diluent.

In some embodiments, the kit further comprises an activation device such as but not limited to a VIALMIX® device.

It also has been found according to the invention that certain of the non-aqueous mixtures (i.e., certain of these modified lipid formulations) may be used to generate lipid-encapsulated gas microspheres, through a process referred to herein as "activation", either as a non-aqueous mixture or following simple addition of aqueous diluent without regard to the degree of homogeneity of the combined solution. This was surprising because certain marketed contrast agents are made by activating a pre-formulated, single-phase mixture comprising lipids in excess aqueous solution. It was not known prior to the invention that lipid-encapsulated microspheres of suitable size and number could be generated without either pre-formulating the lipid in an aqueous solution or in the absence of aqueous solution.

Thus, in another aspect, provided herein is a method of forming an ultrasound contrast agent comprising activating any of the foregoing non-aqueous mixtures in the presence of a perfluorocarbon gas, and in the presence or absence of aqueous diluent, to form lipid-encapsulated gas microspheres.

In another aspect, provided herein is a method of forming an ultrasound contrast agent comprising combining any of the foregoing non-aqueous mixtures with an aqueous diluent in the presence of a perfluorocarbon gas, and activating the combination to form lipid-encapsulated gas microspheres. The aqueous diluent may be added to the non-aqueous mixture with or without agitation or other modification (e.g., heating, etc.), and such combined mixture may be activated, in the presence of a perfluorocarbon gas, regardless of whether it is a single-phase mixture (i.e., the lipid and aqueous phases have been substantially commingled and/or the mixture appears relatively homogeneous) or a double-phase mixture (i.e., the lipid and aqueous phases have not been substantially commingled and/or the mixture does not appear relatively homogeneous).

In another aspect, provided herein is a method of forming an ultrasound contrast agent comprising combining certain of the foregoing non-aqueous mixtures with propylene glycol alone or propylene glycol and an aqueous diluent (simultaneously or consecutively), and activating the combination in the presence of perfluorocarbon gas to form lipid-encapsulated gas microspheres.

In another aspect, provided herein is a method of forming an ultrasound contrast agent comprising combining certain of the foregoing non-aqueous mixtures with glycerol alone or glycerol and an aqueous diluent (simultaneously or consecutively), and activating the combination in the presence of perfluorocarbon gas to form lipid-encapsulated gas microspheres.

The non-aqueous mixtures may be at room temperature and/or may have been stored at room temperature prior to use. Storage at room temperature may have ranged from days, to months, to years.

In some embodiments, activation occurs for 20-45 seconds. In some embodiments, activation occurs for 60-120 seconds.

In some embodiments, the method further comprises diluting the lipid-encapsulated gas microspheres in additional aqueous diluent.

In some embodiments, the method further comprises administering the lipid-encapsulated gas microspheres to a subject in need of contrast ultrasound imaging.

In some embodiments, the composition is in a vial. In some embodiments, the composition is in a syringe. In some embodiments, the composition is in a single chamber container. In some embodiments, the composition is in a multi-chamber container.

In still other aspects, provided herein are methods for detecting and/or measuring levels of impurities in any one of the compositions described herein. Such methods are particularly useful for assessing the integrity of a composition, and may be used to determine that the composition is suitable for use or should be discarded. The methods may be performed on a newly manufactured batch of the compositions described herein, or they may be performed on a batch that has been in transit or in storage for a period of time following its manufacture.

The method comprises detecting and identifying components of the sample. In some embodiments, the method further comprises separating the components based on physicochemical properties such as but not limited to charge and lipophilicity, optionally prior to detection and identification. In some embodiments, separation is performed prior to detection and the sample is diluted with saline prior to separation. In some embodiments, the sample is mixed until a homogenous solution is obtained. Separation techniques based on physicochemical properties are known in the art and include but are not limited to HPLC such as reverse phase HPLC. Impurities are then detected and optionally measured using techniques such as but not limited to charged aerosol detection (CAD). In another embodiment, evaporative light scattering detection (ELSD) may be used following separation. An example of such a detection is described in greater detail herein.

These and other aspects and embodiments of the invention will be described in greater detail herein.

BRIEF DESCRIPTION OF THE FIGURES

FIG. 1. Stability of a lipid blend/propylene glycol (LB/PG) formulation versus DEFINITY®.

FIG. 2. Stability of a lipid blend/propylene glycol/glycerol (LB/PG/G) formulation versus DEFINITY®.

FIG. 3. Stability of a lipid blend/propylene glycol/glycerol/buffer (LB/PG/G/buffer) formulation versus DEFINITY®.

DETAILED DESCRIPTION

It has been found, according to the invention, that lipid formulations for generating lipid-encapsulated gas microspheres to be used as ultrasound imaging agents can be maintained at room temperature, including at room temperature for extended periods of time, without significant degradation. Previously, it was thought that lipid formulations to be used for the same purpose had to be stored at 4° C. in order to avoid degradation. It has been found, according to the invention, that storage of these modified lipid formulations at room temperature for several months results in less than 5% impurities, a level less than that present in a currently marketed ultrasound contrast agent when stored at room temperature for the same period of time.

Importantly, storage of these modified lipid formulations, referred to as lipid-containing non-aqueous mixtures, at room temperature, including long-term storage at room temperature, does not negatively impact their ability to form microspheres for use as ultrasound contrast agents, as evidenced by the ability to form microspheres of size and quantity comparable to currently marketed ultrasound contrast agents. These modified lipid formulations are therefore more robust than certain marketed lipid formulations, at least in view of this enhanced stability.

The new lipid formulations described herein are easier to use than certain existing formulations at least in part because they do not require refrigeration. In contrast, certain currently marketed lipid formulations must be refrigerated throughout their storage period, but then are administered to patients at room temperature. This means that such formulations must first be warmed from about 4° C. to about room temperature before they can be used. In contrast, the modified lipid formulations provided herein can be used essentially "off the shelf" without waiting a required period of time to warm to room temperature. This renders these modified formulations easier to use and also facilitates their immediate use in, for example, emergency situations.

In addition, due to the inherently more robust nature of the modified lipid formulations, there is less chance that their integrity has been compromised prior to use, including for example during transport and storage. In current practice, if certain of the marketed formulations have been stored for any significant period of time at room temperature, then such formulations may be of questionable quality, and thus may need to be discarded. With the new formulations, an end user need not be as concerned about the history or treatment of the formulation. Thus, apart from increased ease of use, there should also be less of the modified lipid formulations wasted due to integrity concerns.

These modified lipid formulations are intended for use as ultrasound contrast agents or as intermediates thereof. As such, and as described herein, when provided together with a gas, they may be activated to form lipid-encapsulated gas microspheres with or without an aqueous diluent. Moreover, when an aqueous diluent is used, such formulations they may be activated following simple addition of the aqueous diluent without any need for pre-formulation or pre-mixing of the non-aqueous mixture and the aqueous diluent. As an example, addition of the aqueous diluent may result in a heterogeneous or two-phase mixture and this two-phase mixture may be activated. Certain marketed ultrasound contrast agents are provided as pre-formulated, relatively homogeneous, single-phase mixtures of lipids formulated in an aqueous matrix, and are activated in this essentially aqueous-formulated form. In contrast, the modified lipid formulations provided herein may be activated in their non-aqueous form or may be activated following simple addition of an aqueous diluent with no requirement for pre-formulation of the lipid(s) and the aqueous diluent or for the mixture to be homogeneous. This in turn means that the lipid formulation volume can be much smaller at the time of activation (and at the time of shipment and storage), and if necessary it can be diluted just prior to use. This also means that the formulation integrity is less likely to be compromised because it is possible to activate without adding an aqueous diluent, and then if the formulation is not used simply store the formulation for later use. If instead the non-aqueous mixture had to be combined with an aqueous solution in order to activate, then this type of flexibility would be lost in this circumstance, and the formulation would have to be discarded, again leading to unnecessary waste.

Accordingly, the invention is based, in part, on the unexpected and surprising finding that lipids used to make lipid-encapsulated gas microspheres, that are themselves suitable as ultrasound contrast agents, when formulated in a non-aqueous mixture, can be stored for extended periods of time at room temperature without significant degradation. The non-aqueous mixture may comprise propylene glycol, or glycerol, or a mixture of propylene glycol and glycerol. Importantly, the lipid formulations provided herein produce lipid-encapsulated gas microspheres on par with those produced by the currently marketed ultrasound contrast agent, DEFINITY®, particularly with respect to microsphere concentration and size, both of which impact the acoustic properties of the microspheres. Such lipid formulations are more robust and insensitive to storage, including long term storage, at room temperature than DEFINITY®.

DEFINITY® is an ultrasound contrast agent that is approved by the FDA for use in subjects with suboptimal echocardiograms to opacify the left ventricular chamber and to improve the delineation of the left ventricular endocardial border. DEFINITY® is provided in a vial comprising a single phase solution comprising DPPA, DPPC and MPEG5000-DPPE in a 10:82:8 mole % ratio in an aqueous solution, and a headspace comprising perfluoropropane gas. Prior to its administration to a subject, DEFINITY® is activated by mechanical shaking (thereafter referred to as "activated DEFINITY®"). Activation results in the formation of a sufficient number of lipid-encapsulated gas microspheres having an average diameter of 1.1 to 3.3 microns. DEFINITY® however must be refrigerated until just prior to use. This limits its utility particularly in settings that lack appropriate refrigeration, particularly during the storage period.

Provided herein are, inter alia, compositions for use in the manufacture of lipid-encapsulated gas microspheres and compositions and uses of the lipid-encapsulated gas microspheres themselves. The invention further provides methods of manufacture of such microspheres.

Storage Formulations

These new formulations comprise a non-aqueous mixture of one or more lipids and propylene glycol (PG), or glycerol (G), or propylene glycol and glycerol (PG/G). It has been found, in accordance with the invention, that these formulations may be stored at higher temperatures for longer periods of time than were previously possible using existing ultrasound contrast agent formulations, without significant degradation. These compositions therefore may be used in a wider range of settings without particular concern about how the formulation was handled prior to use.

The enhanced stability of these new formulations is demonstrated in the Examples, where it is shown that lipid formulations in propylene glycol or propylene glycol and glycerol can be maintained for 3 months or longer with less degradation than is observed in a DEFINITY® formulation maintained at room temperature. The Examples demonstrate that these formulations may be stored for about 3-6 months without significant degradation.

The non-aqueous mixture of lipids in propylene glycol, or glycerol, or propylene glycol and glycerol intends a mixture having less than or equal to 5% water by weight (i.e., weight of water to the weight of the combination of lipids and propylene glycol and/or glycerol). In some instances, the non-aqueous mixture comprises less than 5% water (w/w), 1-4% water (w/w), 1-3% water (w/w), 2-3% water (w/w), or 1-2% water (w/w). In some instances, the non-aqueous mixture comprises less than 1% water (w/w). The water content may be measured at the end of manufacture (and prior to long term storage) or it may be measured after storage, including long term storage, and just before use.

The non-aqueous mixture also may be salt-free intending that it does not contain any salts other than lipid counter-ions. More specifically, and as an example, lipids such as DPPA and DPPE are typically provided as sodium salts. As used herein, a salt-free non-aqueous mixture may comprise such counter-ions (e.g., sodium if DPPA and/or DPPE are used) but they do not contain other ions. In some instances, the non-aqueous mixture is free of sodium chloride or chloride.

The non-aqueous mixture may comprise a buffer. The buffer may be an acetate buffer, a benzoate buffer, or a salicylate buffer, although it is not so limited. Non-phosphate buffers are preferred in some instances due to their dissolution profiles in the non-aqueous mixtures provided herein. In some instances, a phosphate buffer may be used (e.g., following or concurrent with addition of aqueous diluent).

In some embodiments, the non-aqueous mixture comprises, consists of, or consists essentially of (a) one or more lipids, (b) propylene glycol, or glycerol, or propylene glycol/glycerol, and (c) a non-phosphate buffer. Such non-aqueous mixtures may be provided together with a gas such as a perfluorocarbon gas or they may be provided alone (i.e., in the absence of a gas). Such non-aqueous mixtures may be provided in single use amounts and/or in single use containers, with or without a gas. Such containers will typically be sterile.

The non-phosphate buffer may be, but is not limited to, an acetate buffer, a benzoate buffer, a salicylate buffer, a diethanolamine buffer, a triethanolamine buffer, a borate buffer, a carbonate buffer, a glutamate buffer, a succinate buffer, a malate buffer, a tartrate buffer, a glutarate buffer, an aconite buffer, a citric buffer, an acetic buffer, a lactate buffer, a glycerate buffer, a gluconate buffer, and a tris buffer. In some instances, the buffer is a phosphate buffer. It is within the skill of the ordinary artisan to determine and optimize the concentration of buffer for each buffer type.

Room temperature as used herein means a temperature of 15-30° C., including 18-25° C. and 20-25° C., and all temperatures therebetween. The room temperature may be controlled (e.g., maintained thermostatically) to be at such temperature but it is not so limited.

Lipids

These new formulations comprise one and typically more than one lipid. As used herein, "lipids" or "total lipid" or "combined lipids" means a mixture of lipids.

The lipids may be provided in their individual solid state (e.g., powdered) forms. Alternatively, the lipids may be provided as a lipid blend. Methods of making a lipid blend include those described in U.S. Pat. No. 8,084,056 and published PCT application WO 99/36104. A lipid blend, as used herein, is intended to represent two or more lipids which have been blended resulting in a more homogeneous lipid mixture than might otherwise be attainable by simple mixing of lipids in their individual powdered form. The lipid blend is generally in a powder form. A lipid blend may be made through an aqueous suspension-lyophilization process or an organic solvent dissolution-precipitation process using organic solvents. In the aqueous suspension-lyophilization process, the desired lipids are suspended in water at an elevated temperature and then concentrated by lyophilization.

The organic solvent dissolution method involves the following steps:

(a) Contacting the desired lipids (e.g., DPPA, DPPC, and MPEG5000 DPPE) with a first non-aqueous solvent system. This system is typically a combination of solvents, for example $CHCl_3$/MeOH, $CH_2Cl_2$/MeOH, and toluene/MeOH. Preferably, the first non-aqueous solvent is a mixture of toluene and methanol. It may be desirable to warm the lipid solution to a temperature sufficient to achieve complete dissolution. Such a temperature is preferably about 25 to 75° C., more preferably about 35 to 65° C. After dissolution, undissolved foreign matter may be removed by hot-filtration or cooling to room temperature and then filtering. Known methods of filtration may be used (e.g., gravity filtration, vacuum filtration, or pressure filtration).

(b) The solution is then concentrated to a thick gel/semisolid. Concentration is preferably done by vacuum distillation. Other methods of concentrating the solution, such as rotary evaporation, may also be used. The temperature of this step is preferably about 20 to 60° C., more preferably 30 to 50° C.

(c) The thick gel/semisolid is then dispersed in a second non-aqueous solvent. The mixture is slurried, preferably near ambient temperature (e.g., 15-30° C.). Useful second non-aqueous solvents are those that cause the lipids to precipitate from the filtered solution. The second non-aqueous solvent is preferably methyl t-butyl ether (MTBE). Other ethers and alcohols may be used.

(d) The solids produced upon addition of the second non-aqueous solvent are then collected. Preferably the collected solids are washed with another portion of the second non-aqueous solvent (e.g., MTBE). Collection may be performed via vacuum filtration or centrifugation, preferably at ambient temperature. After collection, it is preferred that the solids are dried in vacuo at a temperature of about 20-60° C.

The contents of U.S. Pat. No. 8,084,056 and published PCT application WO 99/36104 relating to the method of generating a lipid blend are incorporated by reference herein.

The organic solvent dissolution-precipitation process is preferred over the aqueous suspension/lyophilization process for a number of reasons as outlined in U.S. Pat. No. 8,084,056 and published PCT application WO 99/36104, including the uniformly distributed lipid solid that results using the organic dissolution method.

Alternatively, the lipids may be provided as individual powders that are dissolved together or individually directly into propylene glycol, glycerol or propylene glycol/glycerol to form the non-aqueous mixture.

As used herein, a lipid solution is a solution comprising a mixture of lipids. Similarly a lipid formulation is a formulation comprising one or more lipids. The lipids may be cationic, anionic or neutral lipids. The lipids may be of either natural, synthetic or semi-synthetic origin, including for example, fatty acids, fluorinated lipids, neutral fats, phosphatides, oils, fluorinated oils, glycolipids, surface active agents (surfactants and fluorosurfactants), aliphatic alcohols, waxes, terpenes and steroids.

At least one of the lipids may be a phospholipid, and thus the lipid blend may be referred to as a phospholipid blend. A phospholipid, as used herein, is a fatty substance containing an oily (hydrophobic) hydrocarbon chain (s) with a polar (hydrophilic) phosphoric head group. Phospholipids are amphiphilic. They spontaneously form boundaries and closed vesicles in aqueous media.

Preferably all of the lipids are phospholipids, preferably 1,2-dipalmitoyl-sn-glycero-3-phosphatidylcholine (DPPC); 1,2-dipalmitoyl-sn-glycero-3-phosphatidic acid (DPPA); and 1,2-dipalmitoyl-sn-glycero-3-phosphatidylethanolamine (DPPE). DPPA and DPPE may be provided as monosodium salt forms.

In some instances, the lipid components may be modified in order to decrease the reactivity of the microsphere with the surrounding environment, including the in vivo environment, thereby extending its half-life. Lipids bearing polymers, such as chitin, hyaluronic acid, polyvinylpyrrolidone or polyethylene glycol (PEG), may also be used for this purpose. Lipids conjugated to PEG are referred to herein as PEGylated lipids. Preferably, the PEGylated lipid is DPPE-PEG or DSPE-PEG Conjugation of the lipid to the polymer such as PEG may be accomplished by a variety of bonds or linkages such as but not limited to amide, carbamate, amine, ester, ether, thioether, thioamide, and disulfide (thioester) linkages.

Terminal groups on the PEG may be, but are not limited to, hydroxy-PEG (HO-PEG) (or a reactive derivative thereof), carboxy-PEG (COOH-PEG), methoxy-PEG (MPEG), or another lower alkyl group, e.g., as in isopropoxyPEG or t-butoxyPEG, amino PEG (NH2PEG) or thiol (SH-PEG).

The molecular weight of PEG may vary from about 500 to about 10000, including from about 1000 to about 7500, and from about 1000 to about 5000. In some important embodiments, the molecular weight of PEG is about 5000. Accordingly, DPPE-PEG5000 or DSPE-PEG5000 refers to DPPE or DSPE having attached thereto a PEG polymer having a molecular weight of about 5000.

The percentage of PEGylated lipids relative to the total amount of lipids in the lipid solution, on a molar basis, is at or between about 2% to about 20%. In various embodiments, the percentage of PEGylated lipids relative to the total amount of lipids is at or between 5 mole percent to about 15 mole percent.

Preferably, the lipids are 1, 2-dipalmitoyl-sn-glycero-3-phosphatidylcholine (DPPC), 1, 2-dipalmitoyl-sn-glycero-3-phosphatidic, mono sodium salt (DPPA), and N-(polyethylene glycol 5000 carbamoyl)-1, 2-dipalmitoyl-sn-glycero-3-phosphatidylethanolamine, monosodium salt (PEG5000-DPPE). The polyethylene glycol 5000 carbamoyl may be methoxy polyethylene glycol 5000 carbamoyl. In some important embodiments, the lipids may be one, two or all three of DPPA, DPPC and PEG5000-DPPE. PEG5000-DPPE may be MPEG5000-DPPE or HO-PEG5000-DPPE.

A wide variety of lipids, like those described in Unger et al. U.S. Pat. No. 5,469,854, may be used in the present process. Suitable lipids include, for example, fatty acids, lysolipids, fluorinated lipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine; dimyristoylphosphatidylcholine; dipentadecanoylphosphatidylcholine; dilauroylphosphatdylcholine; 1,2-dipalmitoyl-sn-glycero-3-phosphatidylcholine (DPPC); distearoylphosphatidylcholine (DSPC); and diarachidonyl-phosphatidylcholine (DAPC); phosphatidylethanolamines, such as dioleoylphosphatidylethanolamine, 1,2-dipalmitoyl-sn-glycero-3-phosphatidylethanolamine (DPPE) and distearoyl-phosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as 1,2-dipalmitoyl-sn-glycero-3-phosphatidic acid (DPPA) and distearoyl-phosphatidic acid (DSPA); palmitic acid; stearic acid; arachidonic acid; and oleic acid.

Other suitable lipids include phosphatidylcholines, such as diolecylphosphatidylcholine, dimyristoylphosphatidylcholine, dipalmitoylphosphatidylcholine (DPPC), and distearoylphosphatidylcholine; phosphatidylethanolamines, such as dipalmitoylphosphatidylethanolamine (DPPE), dioleoylphosphatidylethanolamine and N-succinyl-dioleoyl-phosphatidylethanolamine; phosphatidylserines; phosphatidyl-glycerols; sphingolipids; glycolipids, such as ganglioside GM1; glucolipids; sulfatides; glycosphingolipids; phosphatidic acids, such as dipalmatoylphosphatidic acid (DPPA); palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isopalmitic fatty acids; isostearic fatty acids; cholesterol and cholesterol derivatives, such as cholesterol hemisuccinate, cholesterol sulfate, and cholesteryl-(4'-trimethylammonio)-butanoate; polyoxyethylene fatty acid esters; polyoxyethylene fatty acid alcohols; polyoxyethylene fatty acid alcohol ethers; polyoxyethylated sorbitan fatty acid esters; glycerol polyethylene glycol oxystearate; glycerol polyethylene glycol ricinoleate; ethoxylated soybean sterols; ethoxylated castor oil; polyoxyethylene-polyoxypropylene fatty acid polymers; polyoxyethylene fatty acid stearates; 12-(((7'-diethylaminocoumarin-3-yl)-carbonyl)-methylamino)-octadecanoic acid; N-[12-(((7'-diethylamino-coumarin-3-yl)-carbonyl)-methyl-amino)octadecanoyl]-2-amino-palmitic acid; 1,2-dioleoyl-sn-glycerol; 1,2-dipalmitoyl-sn-3-succinylglycerol; 1,3-dipalmitoyl-2-succinylglycerol; and 1-hexadecyl-2-palmitoyl-glycerophosphoethanolamine and palmitoylhomocysteine; lauryltrimethylammonium bromide (lauryl-=dodecyl-); cetyltrimethylammonium bromide (cetryl-=hexadecyl-); myristyltrimethylammonium bromide (myristyl-=tetradecyl-); alkyldimethylbenzylammonium chlorides, such as wherein alkyl is a C.sub.12, C.sub.14 or C.sub.16 alkyl; benzyldimethyldodecylammonium bromide; benzyldimethyldodecylammonium chloride, benzyldimethylhexadecylammonium bromide; benzyldimethylhexadecylammonium chloride; benzyldimethyltetradecylammonium bromide; benzyldimethyltetradecylammonium chloride; cetyldimethylethylammonium bromide; cetyldimethylethylammonium chloride; cetylpyridinium bromide; cetylpyridinium chloride; N-[1-2,3-dioleoyloxy)-propyl]-N,N,N-trimethylammonium chloride (DOTMA); 1,2-dioleoyloxy-3-(trimethylammonio)propane (DOTAP); and 1,2-dioleoyl-e-(4'-trimethylammonio)-butanoyl-sn-glycerol (DOTB).

In some embodiments where DPPA, DPPC and DPPE are used, their molar percentages may be about 77-90 mole % DPPC, about 5-15 mole % DPPA, and about 5-15 mole % DPPE, including DPPE-PEG5000. Preferred ratios of each lipid include those described in the Examples section such as a weight % ratio of 6.0 to 53.5 to 40.5 (DPPA:DPPC:MPEG5000-DPPE) or a mole % ratio of 10 to 82 to 8 (10:82:8) (DPPA:DPPC:MPEG5000-DPPE).

The lipid concentration in the non-aqueous mixtures intended for long term, room temperature storage may vary depending on the embodiment. In some instances, the lipid concentration may range from about 0.1 mg to about 20 mg per mL of non-aqueous mixture, including about 0.9 mg to about 10 mg per mL of non-aqueous mixture and about 0.9 mg to about 7.5 mg per mL of non-aqueous mixture. In some embodiments, the lipid concentration may range from about 0.94 mg to about 7.5 mg lipid per mL of non-aqueous mixture, including about 1.875 mg to about 7.5 mg lipid per mL of non-aqueous mixture, or about 3.75 mg to about 7.5 mg lipid per mL of non-aqueous mixture. In some instances, the lipid concentration is about 0.94 mg to about 1.875 mg per mL of non-aqueous mixture, about 1.875 mg to about 3.75 mg per mL of non-aqueous mixture, or about 3.75 mg to about 7.5 mg of total lipid per mL of non-aqueous mixture.

As an example, the lipid concentration may range from about 0.1 mg to about 10 mg lipid per mL of propylene glycol/glycerol (combined), including about 1 mg to about 5 mg lipid per mL of propylene glycol/glycerol (combined). In some instances, the lipid concentration is about 0.94 mg to about 3.75 mg lipid per mL of propylene glycol/glycerol (combined).

As another example, the lipid concentration may range from about 0.1 mg to about 20 mg lipid per mL of propylene glycol, including about 1 mg to about 10 mg lipid per mL of propylene glycol, or about 2 mg to about 7.5 mg lipid per mL of propylene glycol, or about 3.75 mg to about 7.5 mg lipid per ml of propylene glycol. In some embodiments, the lipid concentration is about 1.875 mg to about 7.5 mg lipid per mL of propylene glycol, including about 3.75 mg to about 7.5 mg lipid per mL of propylene glycol.

As yet another example, the lipid concentration may range from about 0.1 mg to about 20 mg lipid per mL of glycerol, including about 1 mg to about 10 mg lipid per mL glycerol, or about 2 mg to about 7.5 mg lipid per mL of glycerol, or about 3.75 mg to about 7.5 mg lipid per ml of glycerol. In some instances, the lipid concentration is about 1.875 mg to about 7.5 mg lipid per mL of glycerol, including about 3.75 mg to about 7.5 mg lipid per mL of glycerol.

The ability to generate compositions of lipid-encapsulated gas microspheres that are still useful as ultrasound contrast agents using lower amounts of lipid, as compared to marketed ultrasound contrast agent lipid formulations, is beneficial since it reduces the maximum amount of lipids (and other constituents) that could be administered to a subject from a single vial, thereby reducing the chance of accidental overdosing of a subject.

Propylene glycol is a liquid at room temperature having a density of 1.035 g/ml at 20° C. Glycerol is a liquid at room temperature having a density of 1.26 g/ml at 20° C.

The total volume of the non-aqueous mixtures capable of long term, room temperature storage may range depending on the final intended use. As an example, volumes may range from about 0.05 to about 10 mL, or about 0.1 to about 10 mL, or about 0.1 to about 5 mL, or about 0.25 to about 5 mL, or about 0.5 to about 1 mL, or about 0.1 to about 1.0 mL.

It is to be understood that these non-aqueous mixtures will typically be diluted, for example, with an aqueous solution prior to activation, as described below, and/or prior to administration to a subject. Total dilution may be about 1-fold to about 100-fold, including about 5-fold to about 30-fold, including about 5-fold, about 10-fold, about 20-fold, and about 50-fold.

In some embodiments, the lipid formulations comprising lipid, propylene glycol and glycerol may be diluted about 5-fold prior to activation. In some embodiments, the lipid formulations comprising lipid and propylene glycol may be diluted about 10-fold prior to activation. In some embodiments, the lipid formulations comprising lipid and glycerol may be diluted about 10-fold prior to activation. Thereafter the diluted composition may be further diluted by about 1-fold to about 50-fold, including about 10-fold to about 50-fold, including about 10-fold.

Accordingly, the afore-mentioned lipid, propylene glycol and glycerol concentrations will change upon dilution. For example, in instances where the dilution is about 10-fold, the lipid concentrations of the final formulation are about 10-fold reduced to those recited above. Similar reductions will occur in propylene glycol and/or glycerol concentrations.

Gas

The non-aqueous mixtures may be provided with a gas. For example, the non-aqueous mixtures may be provided in contact with a gas, or they may be provided in the same container or housing as a gas but not in contact with the gas (i.e., the non-aqueous mixture and the gas may be physically separate from each other).

It was not heretofore known or expected that these non-aqueous mixtures could be stably stored long term, at room temperature in contact with a gas such as a perfluorocarbon gas. It was also not known or expected that these non-aqueous mixtures could be activated to form lipid-encapsulated gas microspheres. It was further found in accordance with the invention that certain of these non-aqueous mixtures can be used to form microspheres in sufficient number and of sufficient size (as expressed for example as diameter) to be clinically useful.

The gas is preferably substantially insoluble in the lipid formulations provided herein such as the non-aqueous mixture. The gas may be a non-soluble fluorinated gas such as sulfur hexafluoride or a perfluorocarbon gas. Examples of perfluorocarbon gases include perfluoropropane, perfluoromethane, perfluoroethane, perfluorobutane, perfluoropentane, perfluorohexane. Examples of gases that may be used in the microspheres of the invention are described in U.S. Pat. No. 5,656,211 and are incorporated by reference herein. In an important embodiment, the gas is perfluoropropane.

Examples of gases include, but are not limited to, hexafluoroacetone, isopropylacetylene, allene, tetrafluoroallene, boron trifluoride, 1,2-butadiene, 1,3-butadiene, 1,2,3-trichlorobutadiene, 2-fluoro-1,3-butadiene, 2-methyl-1,3 butadiene, hexafluoro-1,3-butadiene, butadiyne, 1-fluorobutane, 2-methylbutane, decafluorobutane (perfluorobutane), decafluoroisobutane (perfluoroisobutane), 1-butene, 2-butene, 2-methy-1-butene, 3-methyl-1-butene, perfluoro-1-butene, perfluoro-1-butene, perfluoro-2-butene, 4-phenyl-3-butene-2-one, 2-methyl-1-butene-3-yne, butylnitrate, 1-butyne, 2-butyne, 2-chloro-1,1,1,4,4,4-hexafluoro-butyne, 3-methyl-1-butyne, perfluoro-2-butyne, 2-bromo-butyraldehyde, carbonyl sulfide, crotononitrile, cyclobutane, methylcyclobutane, octafluorocyclobutane (perfluorocyclobutane), perfluoroisobutane, 3-chlorocyclopentene, cyclopropane, 1,2-dimethylcyclopropane, 1,1-dimethylcyclopropane, ethyl cyclopropane, methylcyclopropane, diacetylene, 3-ethyl-3-methyldiaziridine, 1,1,1-trifluorodiazoethane, dimethylamine, hexafluorodimethylamine, dimethylethylamine, bis-(dimethyl phosphine)amine, 2,3-dimethyl-2-norbornane, perfluoro-dimethylamine, dimethyloxonium chloride, 1,3-dioxolane-2-one, 1,1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1-chloro-1,1,2,2-tetrafluoro-ethane, 2-chloro-1,1-difluoroethane, chloroethane, chloropentafluoroethane, dichlorotrifluoroethane, fluoroethane, nitropentafluoroethane, nitrosopentafluoro-ethane, perfluoroethane, perfluoroethylamine, ethyl vinyl ether, 1,1-dichloroethylene, 1,1-dichloro-1,2-difluoroethylene, 1,2-difluoroethylene, methane, methane-sulfonyl-chlori-detrifluoro, methane-sulfonyl-fluoride-trifluoro, methane-(pentafluorothio)trifluoro, methane-bromo-difluoro-nitroso, methane-bromo-fluoro, methane-bromochloro-fluoro, methane-bromo-trifluoro, methane-chloro-difluoro-nitro, methane-chloro-dinitro, methane-chlorofluoro, methane-chloro-trifluoro, methane-chloro-difluoro, methane-dibromo-difluoro, methane-dichloro-difluoro, methane-dichloro-fluoro, methane-difluoro, methane-difluoro-iodo, methane-disilano, methane-fluoro, methane-iodomethane-iodo-trifluoro, methane-nitro-trifluoro, methanenitroso-triofluoro, methane-tetrafluoro, methane-trichlorofluoro, methane-trifluoro, methane sulfenylchloride-trifluoro, 2-methyl butane, methyl ether, methyl isopropyl ether, methyl lactate, methyl nitrite, methyl sulfide, methyl vinyl ether, neopentane, nitrogen (N.sub.2), nitrous oxide, 1,2,3-nonadecane tricarboxylic acid-2-hydroxycrimethyl-ester, 1-nonene-3-yne, oxygen (O.sub.2), oxygen 17 (.sup.17 O.sub.2), 1,4-pentadiene, n-pentane, dodecafluoropentane (perfluoropentane), tetradecafluorohexane (perfluorohexane), perfluoroisopentane, perfluoroneopentane, 2-pentanone-4-amino-4-methyl, 1-pentene, 2-pentene {cis}, 2-pentene {trans}, 1-pentene-3-bromo, 1-pentene-perfluoro, phthalic acid-tetrachloro, piperidine-2,3,6-trimethyl, propane, propane-1,1,1,2,2,3-hexafluoro, propane-1,2-epoxy, propane-2,2 difluoro, propane-2-amino, propane-2-chloro, propane-heptafluoro-1-nitro, propane-heptafluoro-1-nitroso, perfluoropropane, propene, propyl-1,1,1,2,3,3-hexafluoro-2, 3 dichloro, propylene-1-chloro, propylene-chloro-{trans}, propylene-2-chloro, propylene-3-fluoro, propylene-perfluoro, propyne, propyne-3,3,3-trifluoro, styrene-3-fluoro, sulfur hexafluoride, sulfur (di)-decafluoro(S.sub.2 F.sub.10), toluene-2,4-diamino, trifluoroacetonitrile, trifluoromethyl peroxide, trifluoromethyl sulfide, tungsten hexafluoride, vinyl acetylene, vinyl ether, neon, helium, krypton, xenon (especially rubidium enriched hyperpolarized xenon gas), carbon dioxide, helium, and air.

Fluorinated gases (that is, a gas containing one or more fluorine molecules, such as sulfur hexafluoride), fluorocarbon gases (that is, a fluorinated gas which is a fluorinated carbon or gas), and perfluorocarbon gases (that is, a fluorocarbon gas which is fully fluorinated, such as perfluoropropane and perfluorobutane) are preferred.

The gas such as the perfluorocarbon gas is typically present below its ordinary concentration at room temperature due to the incorporation of air during production. The concentration of perfluoropropane when present in a vial comprising a non-aqueous mixture and a gas headspace is expected to be about 6.52 mg/mL, at about one atmosphere of pressure. The concentrations of other gases, as known in the art, would be similarly diluted due to incorporation of air during production.

The invention contemplates that the non-aqueous mixtures provided herein, whether in contact with or physically separate from a gas such as a perfluorocarbon gas, may be stored at a temperature in the range of about 4° C. to about 40° C., about 4° C. to about 30° C., about 4° C. to about 25° C., about 10° C. to about 40° C., about 15° C. to about 40° C., or about 15° C. to about 30° C.

The invention further contemplates that the non-aqueous mixtures provided herein, whether in contact with or physically separate from a gas such as a perfluorocarbon gas, may be stored for about 1 month to about 6 months, about 1 month to about 1 year, or about 1 month to about 2 years. Thus, the non-aqueous mixtures provided herein, whether in contact with or physically separate from a gas such as a perfluorocarbon gas, may be stored for about 1 month to about 2 years at a temperature range of about 15° C. to about 30° C., as a non-limiting example.

Containers and Chamber Configurations

The non-aqueous mixtures may be provided in a container (or housing). The container may be a single chamber or a multi-chamber container, such as but not limited to a dual chamber container.

In some embodiments, the container is a vial. The vial may be made of any material including but not limited to glass or plastic. The glass may be pharmaceutical grade glass. The container may be sealed with a stopper such as a rubber stopper. In some embodiments, the container is a 0.5-10 mL container. The container may be a 1-5 mL container, or a 1 or 2 mL container. Such volumes refer to the volume of liquid typically placed into the container (referred to as the liquid fill volume). This is in contrast to the entire internal volume of the container, which will be higher than the liquid fill volume. Examples of liquid fill and internal volumes are as follows: Schott 2 mL (liquid fill volume) vial having a 2.9 mL internal volume; Schott 3 mL (liquid fill volume) vial having a 4.5 mL internal volume; and Wheaton 1 mL (liquid fill volume) v-vial having a 1.2 mL internal volume.

As will be understood in the context of this disclosure, the internal volume of a container may be occupied with non-aqueous mixture and gas. An example of a suitable container is the Wheaton 2 ml glass vial (commercially available from, for example, Nipro, Cat. No. 2702, B33BA, 2 cc, 13 mm, Type I, flint tubing vial), having an actual internal volume of about 3.75 ml. An example of a suitable stopper is a West gray butyl lyo, siliconized stopper (Cat. No. V50, 4416/50, 13 mm). An example of a suitable seal is a West flip-off aluminum seal (Cat. No. 3766, white, 13 mm). The containers are preferably sterile and/or are sterilized after introduction of the lipid solution and/or gas as described in published PCT application WO99/36104.

In some embodiments, the container is a flat bottom container such as a flat-bottom vial. Suitable vials include flat bottom borosilicate vials, including Wheaton vials. In some embodiments, the container is a non-flat bottom container or vial. In some embodiments, the container is a V-bottom container such as a V-bottom vial. In some embodiments, the container is a round-bottom container such as round-bottom vial. In some embodiments, the container has converging walls such that its bottom surface area (or bottom surface diameter) is smaller than its top (opening) surface area (or diameter) or smaller than any diameter therebetween (e.g., a body diameter). For clarity, a V-bottom container or vial has converging walls, and its bottom surface area is significantly smaller than any of it top or body surface areas.

In some embodiments, the container is a syringe. The non-aqueous mixture may be provided in a pre-filled syringe, optionally in physical contact with the gas.

In some embodiments, the container is a single chamber container, such as a vial. In such a single chamber, the non-aqueous mixture and the gas, if present, may be in physical contact with each other.

In some embodiments, the containers comprise two or more chambers. The contents of the two chambers are physically separated from each other, for example during storage. However, when used, the contents of the two chambers are combined and intermingled. Thus, the container further comprises a barrier that physically separates the contents of the first and second chambers but that can be "removed" in order to combine those contents ultimately. The disclosure contemplates any possible means of removing such barrier including pressure, mechanical piercing or punching, dissolution, and the like.

Dual chamber devices such as dual chamber syringes or dual chamber tubes are known in the art and are commercially available. Non-limiting examples include Vetter dual chamber syringes and NeoPak dual chamber tubes.

In some embodiments, a non-aqueous mixture consisting of or consisting essentially of one or more lipids, propylene glycol, or glycerol, or propylene glycol/glycerol, and a non-phosphate buffer is provided in a container such as a single chamber container. Such a mixture may be provided with or without a gas such as a perfluorocarbon gas. If provided with the gas, the gas may be in the same chamber as the non-aqueous mixture or in a separate chamber of a multi-chamber container, as provided below.

The container may have two chambers, wherein a first chamber comprises the non-aqueous mixture comprising the lipid(s) such as DPPA, DPPC and PEG5000-DPPE in propylene glycol and glycerol or propylene glycol or glycerol, and a second chamber comprises a gas such as a perfluorocarbon gas. The non-aqueous mixture may comprise a buffer such as a non-phosphate buffer.

In another embodiment, the container may have two chambers, wherein a first chamber comprises
 (i) the non-aqueous mixture comprising
  (a) the lipid(s) such as DPPA, DPPC and PEG5000-DPPE and
  (b) propylene glycol and glycerol or propylene glycol or glycerol, and
 (ii) a gas such as a perfluorocarbon gas, and a second chamber comprises an aqueous diluent.

The non-aqueous mixture may comprise a buffer such as a non-phosphate buffer. Alternatively, the aqueous solution may comprise a buffer such as a phosphate buffer.

In another embodiment, the container may have two chambers, wherein a first chamber comprises
 (i) the non-aqueous mixture comprising
  (a) the lipid(s) such as DPPA, DPPC and PEG5000-DPPE and
  (b) propylene glycol and glycerol or propylene glycol or glycerol, and a second chamber comprises
 (i) an aqueous diluent, and
 (ii) a gas such as a perfluorocarbon gas.

In another embodiment, the container may have at least three chambers, wherein a first chamber comprises a non-aqueous mixture comprising DPPA, DPPC and PEG5000-DPPE in propylene glycol or glycerol or propylene glycol and glycerol, a second chamber comprises a gas such as a perfluorocarbon gas, and a third chamber comprises an aqueous solution.

In another embodiment, the container may comprise a first chamber that comprises the non-aqueous mixture comprising lipids and propylene glycol and a second chamber that comprises glycerol. In another embodiment, the container may comprise a first chamber that comprises the non-aqueous mixture comprising lipids and glycerol and a second chamber that comprises propylene glycol.

The aqueous diluent may comprise salts such as but not limited to sodium chloride, and thus may be regarded as a saline solution. The aqueous diluent may comprise a buffer such as a phosphate buffer, and thus may be regarded as a buffered aqueous diluent. The aqueous diluent may be a buffered saline solution. The non-aqueous mixture may comprise a buffer such as a non-phosphate buffer, examples of which are provided herein. The non-aqueous mixture and the aqueous diluent may both comprise a buffer. In typical embodiments, either the non-aqueous mixture or the aqueous diluent comprises a buffer, but not both. The buffer concentration will vary depending on the type of buffer used, as will be understood and within the skill of the ordinary artisan to determine. The buffer concentration in the non-aqueous lipid formulation may range from about 1 mM to about 100 mM. In some instances, the buffer concentration may be about 1 mM to about 50 mM, or about 1 mM to about 20 mM, or about 1 mM to about 10 mM, or about 1 mM to about 5 mM, including about 5 mM.

The final formulation to be administered typically intravenously to a subject including a human subject may have a pH in the range of 4-8 or in a range of 4.5-7.5. In some instances, the pH may be in a range of about 6 to about 7.5, or in a range of 6.2 to about 6.8. In still other instances, the pH may be about 6.5 (e.g., 6.5+/−0.5 or +/−0.3). In some instances, the pH may be in a range of 5 to 6.5 or in a range of 5.2 to 6.3 or in a range of 5.5 to 6.1 or in a range of 5.6 to 6 or in a range of 5.65 to 5.95. In still another instance, the pH may be in a range of about 5.7 to about 5.9 (e.g., +/−0.1 or +/−0.2 or +/−0.3 either or both ends of the range). In another instance, the pH may be about 5.8 (e.g., 5.8+/−0.15 or 5.8+/−0.1).

In some embodiments, the aqueous diluent comprises glycerol, a buffer such as phosphate buffer, salt(s) and water. Such an aqueous diluent may be used with a non-aqueous mixture that lacks glycerol. In some embodiments, the lipid solution further comprises saline (salt(s) and water combined) and glycerol in a weight ratio of 8:1.

In some embodiments, the aqueous diluent comprises propylene glycol, a buffer such as phosphate buffer, salt(s) and water. Such an aqueous diluent may be used with a non-aqueous mixture that lacks propylene glycol.

In some embodiments, the aqueous diluent comprises a buffer such as phosphate buffer, salt(s) and water. Such an aqueous diluent may be used with a non-aqueous mixture that comprises both propylene glycol and glycerol.

Provided herein is a method comprising placing a non-aqueous mixture of lipids and propylene glycol, and a gas into a container, a method comprising placing a non-aqueous mixture of lipids and glycerol, and a gas into a container, and a method comprising placing a non-aqueous mixture of lipids and propylene glycol and glycerol, and a gas into a container. In any of these methods, the gas may be placed into the container through exchange of the headspace gas. Gas exchangers suitable for this purpose are known in the art. An example of a gas exchange device is a lyophilizing chamber. Such containers may then be stored at about 10 to about 50° C., or about 15 to about 40° C., or about 20 to about 30° C. for up to 2 years, or for 1 to 12 months, or for 1-30 days. In another aspect, the container may be provided with instructions for storage at the foregoing temperatures, optionally for the foregoing periods of time, or alternatively lacking instructions for storage at 4° C. or under refrigeration.

Provided herein is a method comprising combining a first composition comprising a non-aqueous solution of lipids in propylene glycol and perfluorocarbon gas with a second composition comprising an aqueous diluent, a method comprising combining a first composition comprising a non-aqueous solution of lipids in glycerol and perfluorocarbon gas with a second composition comprising an aqueous diluent, and a method comprising combining a first composition comprising a non-aqueous solution of lipids in propylene glycol and glycerol and perfluorocarbon gas with a second composition comprising an aqueous diluent.

The first and second compositions may be provided in first and second chambers of a container, respectively, and combining may comprise breaking a seal between the first and second chambers. The first composition may be provided in a vial and the second composition may be provided in a syringe, with the contents of the syringe being added to the contents of the vial. Alternatively, the second composition may be provided in a vial and the first composition may be provided in a syringe, with the contents of the syringe being added to the contents of the vial.

It is to be understood that any combination or variation on the foregoing embodiments is contemplated and embraced by this disclosure, and that the foregoing examples are not to be considered limiting unless expressly indicated.

Any of the foregoing container embodiments may be provided, with or without an additional housing, with instructions for storage at a temperature above 4° C. (or without refrigeration) or with instructions that are silent regarding storage temperature. It is to be understood that the formulations provided herein may be stored at 4° C. but there is no requirement that they be stored at this temperature. The instructions may further recite long term storage such as storage for days, months or even years and may further recite that long term storage occur at or about room temperature (e.g., 18-25° C.).

In some embodiments, the composition is in a container, such as a vial, and such container is labeled. The container may have a label affixed to one or more of its outer surfaces. Such label may be a paper label or other such label that is visible by eye and capable of being read and understood by an end user without further aid or device. Alternatively, the label may be one that is machine- or device readable. Examples of machine- or device-readable labels include magnetic stripes, chips, barcodes including linear, matrix and 2D barcodes, radio frequency identification (RFID) tags, and the like. Barcodes such as linear barcodes may be those that comply with or meet Uniform Code Council standards or Health Industry Business Communications Council standards. Such labels may in turn be read, for example, from a device such as a magnetic stripe reader, a chip reader, a barcode scanner or reader, an RFID tag reader, and the like. Virtually any labeling technology that has been used for authentication and/or "track and trace" purposes may be used in conjunction with the containers provided herein.

The label may provide the end user or an intermediate handler of the container a variety of information including but not limited to source and/or producer of the composition contained therein, including for example the name of the company or company subsidiary that made the composition and/or that produced components of the composition, the date on which the composition was made, the physical location where the composition was made, the date of shipment of the container, the treatment of the container including for example whether it was stored in a remote location and the conditions and length of such storage, the date on which the container was delivered, the means of delivery, the National Drug Code (NDC) as prescribed by the FDA, content of the container, dose and method of use including route of administration, etc.

The label may serve one or more purposes including for example authentication of the container and the composition contained therein. Authentication means the ability to identify or mark the container as originating and having been made by an authorized party, and it allows an end user or other party to identify container and compositions originating from another, unauthorized party. The label may also be used to track and trace a container. This feature can be used to follow a container and the composition contained therein following production and up to the point of administration to a subject. In this regard, the movement of the container during that period of time may be stored in a database, and optionally such database may be accessible to an end user to ensure the integrity of the composition.

The label may also be a combined label, intending that it may contain information that is read using two different modes. For example, the label may contain information that is apparent and understandable to the visible eye (e.g., it may recite the name of the producer in words) and other information that is machine-readable, such as RFID embedded or barcode embedded information.

The label may also be a dual use label, intending that it may serve two or more purposes. For example, the label may contain information that identifies the composition and further information that identifies the manufacturer and/or date of manufacture. This information may be conveyed in the same format or using different format (e.g., one may be provided in an RFID label and the other may be provided in a barcode label).

The label may provide content that is visible and understandable to a human, such as for example the name of the manufacturer. Alternatively or additionally, the label may contain information that while readily visible to the human eye nevertheless provides no meaningful information in the absence of a lookup table or other form of database to which reference must be made. Such information for example may be provided as alpha-numeric code.

Activation

Any of the foregoing compositions may be used to form lipid-encapsulated gas microspheres which in turn can be used as an ultrasound contrast agent. As used herein, lipid-encapsulated gas microspheres are spheres having an internal volume that is predominantly gas and that is encapsulated by a lipid shell. The lipid shell may be arranged as a unilayer or a bilayer, including unilamellar or multilamellar bilayers. These microspheres are useful as ultrasound contrast agents.

Microspheres are generated from the non-aqueous mixtures through a process of activation. Activation, as described in greater detail herein, refers to a vigorous shaking of a lipid solution (such as a non-aqueous solution) for the purpose of producing lipid-encapsulated gas microspheres. Activation typically produces at least $1 \times 10^7$ microspheres per ml of solution, $5 \times 10^7$ microspheres per ml of solution, or at least $7.5 \times 10^7$ microspheres per ml of solution, or at least $1 \times 10^8$ microspheres per ml of solution, or about $1 \times 10^9$ microspheres per ml of solution.

The disclosure contemplates that certain non-aqueous mixtures provided herein can be used to form lipid-encapsulated gas microspheres in the presence of a gas. It was unexpected that these non-aqueous mixtures could be activated.

Activation may be performed by vigorous agitation including shaking for a defined period of time. As described above, activation may occur in the presence or absence of an aqueous diluent. Activation, as used herein, is defined as a motion that agitates a lipid solution such that a gas is introduced from the headspace into the lipid solution. Any type of motion that agitates the lipid solution and results in the introduction of gas may be used for the shaking. The agitation must be of sufficient force to allow the formation of foam after a period of time. Preferably, the agitation is of sufficient force such that foam is formed within a short period of time, such as 30 minutes, and preferably within 20 minutes, and more preferably, within 10 minutes. In some embodiments, activation can occur in less than 5 minutes, less than 4 minutes, less than 3 minutes, less than 2 minutes, in about 75 seconds, less than a minute, or in about 45 seconds. The agitation may be by microemulsifying, by microfluidizing, for example, swirling (such as by vortexing), side-to-side, or up and down motion. Different types of motion may be combined. The agitation may occur by shaking the container holding the lipid solution, or by shaking the lipid solution within the container without shaking the container itself. Further, the shaking may occur manually or by machine. Mechanical shakers that may be used include, for example, a shaker table, such as a VWR Scientific (Cerritos, Calif.) shaker table, a microfluidizer, Wig-L-Bug™ (Crescent Dental Manufacturing, Inc., Lyons, Ill.), and a mechanical paint mixer, VIALMIX®, or any of the devices described in Example 12 Vigorous shaking is defined as at least about 60 shaking motions per minute. This is preferred in some instances. Vortexing at at least 1000 revolutions per minute is an example of vigorous shaking and is more preferred in some instances. Vortexing at 1800 revolutions per minute is even more preferred in some instances.

VIALMIX® is described in U.S. Pat. No. 6,039,557. Containers such as vials may be sufficiently agitated using VIALMIX® for the ranges of times recited above, including for example 45 seconds. Activation using VIALMIX® may occur for less than 1 minute or longer, including for 30 seconds, 45 seconds, 60 seconds, 75 seconds, 90 seconds, 105 seconds, 120 seconds or longer.

Further examples of activation methods are provided in Example 12.

Non-aqueous mixtures comprising lipids and propylene glycol and glycerol may be activated in the presence of a gas without addition of other solutions. Alternatively, this mixture may be first combined with an aqueous diluent, and then activated in the presence of a gas.

Non-aqueous mixtures comprising of lipids and propylene glycol may be first combined with glycerol, and optionally an aqueous diluent, and then activated in the presence of a gas.

Non-aqueous mixtures comprising lipids and glycerol may be first combined with propylene glycol, and optionally an aqueous diluent, and then activated in the presence of a gas.

In other instances, the lipids in solid form, whether as a lipid blend or not, may be dissolved in propylene glycol alone or glycerol alone or in propylene glycol and glycerol or in propylene glycol, glycerol and an aqueous diluent that may in turn comprise salt(s) and buffer. Any one of these mixtures may be activated, and in some instances, may be further diluted with an aqueous diluent, prior to use.

Thus provided herein is a composition comprising lipid-encapsulated gas microspheres comprising DPPA, DPPC and PEG5000-DPPE in a non-aqueous mixture comprising propylene glycol and glycerol and a perfluorocarbon gas, a composition comprising lipid-encapsulated gas microspheres comprising DPPA, DPPC and PEG5000-DPPE in a non-aqueous mixture comprising propylene glycol and a perfluorocarbon gas, and a composition comprising lipid-encapsulated gas microspheres comprising DPPA, DPPC and PEG5000-DPPE in a non-aqueous mixture comprising glycerol and a perfluorocarbon gas.

The disclosure also contemplates formation of the microspheres in the presence of an aqueous diluent such as but not limited to an aqueous buffered saline solution. The aqueous diluent may comprise salt(s), buffer(s), propylene glycol, glycerol and water.

In some embodiments, an activated composition comprising lipid-encapsulated gas microspheres may comprise saline, glycerol and propylene glycol is a weight % ratio of 8:1:1.

Once formed, the microspheres may be diluted in an aqueous diluent, and then administered to a subject. The aqueous saline solution will typically be pharmaceutically acceptable and may lack preservatives (being referred to herein as preservative-free). The aqueous diluent may be a saline solution (i.e., it may contain salt such as but not limited to sodium chloride) and/or it may contain a buffer such as but not limited to a phosphate buffer. The lipid-encapsulated gas microspheres may be diluted by about 5 to about 50 fold, or about 35 to about 45 fold. The diluted lipid-encapsulated gas microspheres may be administered by bolus or continuous infusion into a subject in need of ultrasound contrast imaging.

The microspheres have an average diameter in the micron range. In some embodiments, the microspheres have an average diameter ranging from about 1.0 to about 2.0 microns, or about 1.2 microns to about 1.8 microns. In some embodiments, the microspheres have an average diameter of about 1.6 microns.

In some embodiments, a majority of the microspheres may have a diameter in the range of about 1.0 to about 3.0 microns, or about 1.0 to about 2.0 microns, or about 1.2 to about 2.0 microns, preferably in the range of about 1.2 to about 1.8 microns. The majority of microspheres means at least 50%, preferably at least 75%, more preferably at least 80%, and even more preferably at least 90% of the measured lipid-encapsulated gas microspheres in the composition. In some embodiments, at least 50%, or at least 60%, or at least 70%, or at least 80%, at least 90%, or at least 95% of the detected lipid-encapsulated gas microspheres in the composition have a diameter in any of the foregoing ranges.

An average diameter represents the average diameter of all detected microspheres in a composition. Microsphere diameter is typically measured using instrumentation known and available in the art including but not limited to a Malvern FPIA-3000 Sysmex particle sizer. As will be understood in the art, such instrumentation typically has cutoff sizes for both the lower and upper limits. This means that microspheres below or above these cutoffs, respectively, are not counted (and are not included in the microsphere concentration calculation) and their diameter is not measured (and is not taken into consideration in determining the average diameter of microspheres). The instrumentation used in the Examples had a 1.0 micron lower limit cutoff and a 40.0 micron upper limit cutoff. The majority of counted or detected microspheres, using a lower cutoff of 1.0 micron and an upper cutoff of 40.0 microns, have a diameter in the range of 1.0 to 20.0 microns. It is to be understood that this disclosure uses the terms microsphere size and microsphere diameter interchangeably. Thus, unless otherwise specified, microsphere size refers to microsphere diameter.

The composition provided herein including the activated compositions may further comprise other constituents such as stabilizing materials or agents, viscosity modifiers, tonicity agents, coating agents, and suspending agents. Examples of each class of agents are known in the art and are provided in for example U.S. Pat. No. 5,656,211, in published PCT application WO99/36104, and in published US application US 2013/0022550.

The composition provided herein including the activated compositions may comprise one or more buffers including but not limited to acetate buffer, benzoate buffer, salicylate buffer, and/or phosphate buffer.

The pH of the composition may be about 6.2 to about 6.8. In some instances, the pH may be in a range of 5 to 6.5 or in a range of 5.2 to 6.3 or in a range of 5.5 to 6.1 or in a range of 5.6 to 6 or in a range of 5.65 to 5.95. In still another instance, the pH may be in a range of about 5.7 to about 5.9 (e.g., +/−0.1 or +/−0.2 or +/−0.3 either or both ends of the range). In another instance, the pH may be about 5.8 (e.g., 5.8+/−0.15 or 5.8+/−0.1). Such ranges may be achieved, for example, using an acetate buffered formulation diluted in water.

In some embodiments, each ml of the final composition (following dilution of the non-aqueous solution with an aqueous diluent) comprises 0.75 mg of lipids (consisting of 0.045 mg DPPA, 0.401 mg DPPC, and 0.304 mg DPPE-PEG5000), 103.5 mg propylene glycol, 126.2 mg glycerol, 2.34 mg sodium phosphate monobasic monohydrate, 2.16 mg sodium phosphate dibasic heptahydrate, and 4.87 mg sodium chloride in water.

In some embodiments, each ml of final composition comprises about 0.43 mg of lipids (consisting of 0.0225 mg DPPA, 0.2 mg DPPC, and 0.152 mg DPPE-PEG5000), 103.5 mg propylene glycol, 126.2 mg glycerol, 2.34 mg sodium phosphate monobasic monohydrate, 2.16 mg sodium phosphate dibasic heptahydrate, and 4.87 mg sodium chloride in water.

In some embodiments, each ml of the final composition (following dilution of the non-aqueous solution with saline) comprises 0.75 mg of lipids (consisting of 0.045 mg DPPA, 0.401 mg DPPC, and 0.304 mg DPPE-PEG5000), 103.5 mg propylene glycol, 126.2 mg glycerol, 0.074 mg sodium acetate, 0.006 mg acetic acid, and 7.20 mg sodium chloride in water.

Impurities and Stability

The invention further provides a method for assessing impurity content in a lipid solution such as a non-aqueous solution. Such a method comprises analyzing a lipid solution for the presence of impurities using any of a number of analytical methods such as but not limited to charged aerosol detection (CAD) optionally coupled with one or more separation techniques such as HPLC. The lipid solution may be a non-aqueous solution comprising lipids and propylene glycol or glycerol or propylene glycol and glycerol. The lipid solution may further comprise a buffer such as a non-phosphate buffer. The lipid solution may further comprise salt(s) and/or water. The presence of an impurity above a threshold level may signify that the lipid solution was not stored properly, that its stability has been compromised, and thus that the lipid solution should be discarded and not administered to a subject. Such a method could be used for quality control purposes.

Example 2 provides a method for measuring impurity content in a non-aqueous solution. The impurity content is provided as a % impurity relative to the input (or theoretical or nominal) lipid amount, meaning the impurity is expressed as a percentage of the total amount of lipid present assuming no loss of lipid.

The modified lipid formulations may comprise less than 10%, less than 5%, or less than 2% impurities when stored at room temperature for a period of time, including for example, about 1 month, about 2 months, about 3 months, about 6 months, or longer including about 1 year, or about 2 years.

Significantly, the modified lipid formulations may comprise fewer impurities than DEFINITY® when both formulations are stored at room temperature (i.e., when the composition and DEFINITY® are stored at room temperature). This reduction in impurity level may be a difference of about 1%, about 2%, about 3%, about 4%, or about 5%, or more.

Uses and Applications

The invention provides methods of use of the microspheres and microsphere compositions. The microspheres are intended as ultrasound contrast agents, and they may be used in vivo in human or non-human subjects or in vitro. The compositions of the invention may be used for diagnostic or therapeutic purposes or for combined diagnostic and therapeutic purposes.

When used as ultrasound contrast agents for human subjects, the compositions are activated as described herein in order to form a sufficient number of microspheres, optionally diluted into a larger volume, and administered in one or more bolus injections or by a continuous infusion. Administration is typically intravenous injection. Imaging is then performed shortly thereafter. The imaging application can be directed to the heart or it may involve another region of the body that is susceptible to ultrasound imaging. Imaging may be imaging of one or more organs or regions of the body including without limitation the heart, blood vessels, the cardiovasculature, and the liver.

Subjects of the invention include but are not limited to humans and animals. Humans are preferred in some instances.

The lipid compositions are administered in effective amounts. An effective amount will be that amount that facilitates or brings about the intended in vivo response and/or application. In the context of an imaging application, such as an ultrasound application, the effective amount may be an amount of lipid microspheres that allow imaging of a subject or a region of a subject.

EXAMPLES

Example 1. Sample Preparation

The commercial, FDA approved, ultrasound contrast agent, DEFINITY® (Lantheus Medical Imaging) was used for comparison. Each vial contains the following: 1,2-dipalmitoyl-sn-glycero-3-phosphatidylcholine (DPPC; 0.401 mg/mL), 1,2-dipalmitoyl-sn-glycero-3-phosphatidic acid (DPPA; 0.045 mg/mL), and N-(methoxypolyethylene glycol 5000 carbamoyl)-1,2-dipalmitoyl-sn-glycero-3-phosphatidylethanolamine (MPEG5000 DPPE; 0.304 mg/mL) in a matrix of 103.5 mg/mL propylene glycol, 126.2 mg/mL glycerol, and 2.34 mg/mL sodium phosphate monobasic monohydrate, 2.16 mg/mL sodium phosphate dibasic heptahydrate, and 4.87 mg/mL sodium chloride in Water for Injection. The pH is 6.2-6.8. The nominal fill volume of the lipid solution is approximately 1.76 mL in a 2 cc Wheaton glass vial with an approximate volume of 3.80 mL and thus a head space of approximately 2.04 mL containing perfluoropropane gas (PFP, 6.52 mg/mL).

New formulations were prepared as follows:

Lipid blend (LB) containing DPPC, DPPA, MPEG500 DPPE was prepared as described in U.S. Pat. No. 8,084,056, the content of which are hereby incorporated by reference and may be used in the present process. Formulations of LB were prepared by mixing LB powder in propylene glycol (PG), or 1:1 v/v propylene glycol/glycerol (PG/G), or glycerol vehicle at 55° C. In some studies, 0.005 M acetate, benzoate, or salicylate buffer prepared at salt to acid ratios of 90/10, 75/25, 50/50, 25/79 and 10/90 were dissolved in the vehicle. In some instances, phosphate buffer was included in an aqueous or saline solution.

Example 2. Lipid Stability

New formulation lipid blend samples from Example 1 in propylene glycol were placed into 2 cc Wheaton glass vials, the headspace replaced with PFP gas, a West, grey butyl lyo stopper inserted and the vial crimped with an aluminum seal. Vials were stored in an environmental chamber at 25° C. to represent room temperature storage or heated to 130° C. in a drying oven to represent terminal sterilization. At appropriate time points, sample vials were removed from storage, de-crimped, saline was added to the vial and mixed to ensure a homogenous solution. The sample was transferred to a HPLC vial and analyzed by reverse phase HPLC separation and Corona Charged aerosol detection (CAD; HPLC With Charged Aerosol Detection for the Measurement of Different Lipid Classes, I. N. Acworth, P. H. Gamache, R. McCarthy and D. Asa, ESA Biosciences Inc., Chelmsford, Mass., USA; J. Waraska and I. N. Acworth, American Biotechnology Laboratory, January 2008) for impurities.

Results for DEFINITY® vials stored 3 months at 25° C. are provided for comparison. Analysis used gradient reverse phase HPLC with Evaporative Light Scattering Detection, (ELSD) using a C18 column and mobile phase containing: water, methanol, ammonium acetate, and triethylamine. Tables 1 and 2, provide the total impurity as a percentage of the total lipid content in the vial at 25° C. and 130° C.

TABLE 1

Impurity data for lipid blend (LB) in propylene glycol (PG) formulation stored at 25° C.

| | 7.50 mg Lipid Blend/mL PG* | DEFINITY® (0.75 mg Lipid Blend/mL) |
|---|---|---|
| Number of Days at 25° C. | 96 days (approximately 3 months) | 3 months |
| PERCENT TOTAL IMPURITY | 2.1 | 11.86 |

*177 mg of PG containing LB (0.72 wt % LB; ratio of 1:138 for LB:PG).

TABLE 2

Impurity data for lipid blend (LB) in propylene glycol (PG) formulation and DEFINITY® processed at 130° C. for 30 minutes

| | 7.50 mg Lipid Blend/mL PG* | 3.75 mg Lipid Blend/mL PG** | DEFINITY® (0.75 mg Lipid Blend/mL) |
|---|---|---|---|
| PERCENT TOTAL IMPURITY | 0.334 | 0.818 | 4.230 |

*89 mg of PG containing LB (0.72 wt % LB; ratio of 1:138 for LB:PG).
**177 mg of PG containing LB (0.36 wt % LB; ration of 1:276 for LB:PG).

FIG. 1 illustrates the total impurity levels as a function of time for DEFINITY® at 2-8° C. and 25° C. and for the 7.5 mg LB/mL PG at 25° C. The total impurity level in DEFINITY® stored at 2-8° C. was similar to that of the 7.5 mg LB/mL PG formulation stored at 25° C. When DEFINITY® was stored at 25° C., however, the level of total impurities dramatically increased.

These data demonstrate that the 7.5 mg LB/mL PG formulation is far more robust than the DEFINITY® formulation at higher temperatures. This observation was unexpected.

Example 3. Stability of Lipid Blend/Propylene Glycol/Glycerol (LB/PG/G) Formulation New formulation lipid blend sample from Example 1 in 1:1 (v:v) propylene glycol/glycerol was filled into a 2 cc Wheaton glass vial, the headspace replaced with PFP gas, a West, grey butyl lyo stopper, inserted and the vial crimped with an aluminum seal. Vials were stored in an environmental chamber at 25° C. to represent room temperature storage or heated to 130° C. in an oven to represent terminal sterilization. Vials stored at 25° C. were prepared and analyzed as described in Example 2. Vials heated at 130° C. were prepared as described in Example 2, but were analyzed using the HPLC system as described for DEFINITY® in Example 2. Table 3 and 4, provide the total impurity as a percentage of the total lipid content in the vial at 25° C. and 130° C. Results for DEFINITY® analyzed as described in Example 2 are provided for comparison.

TABLE 3

Impurity data for 3.75 mg lipid blend (LB) per mL in PG/G formulation stored at 25° C.

|  | 3.75 mg Lipid Blend/mL PG/G* | DEFINITY® (0.75 mg Lipid Blend/mL) |
|---|---|---|
| Number of Days at 25° C. | 87 days (approximately 3 months) | 3 months |
| PERCENT TOTAL IMPURITY | 1.747 | 11.86 |

*391 mg of PG/G containing LB (0.33 wt % LB: 44.9 wt % PG: 54.8 wt % G; ratio of 1:138:168 for LB:PG:G).

TABLE 4

Impurity data for lipid blend (LB) in PG/G formulations and DEFINITY® processed at 130° C. for 30 minutes

|  | 3.75 mg Lipid Blend/mL PG/G* | DEFINITY® (0.75 mg Lipid Blend/mL) |
|---|---|---|
| PERCENT TOTAL IMPURITY | 2.558 | 4.150 |

*391 mg of PG/G containing LB (0.33 wt % LB: 44.9 wt % PG: 54.8 wt % G; ratio of 1:138:168 for LB:PG:G).

FIG. 2 illustrates the total impurity levels as a function of time for DEFINITY® stored at 2-8° C. and 25° C. and for the 3.75 mg LB/mL PG/G formulation stored at 25° C. The total impurity level in DEFINITY® stored at 2-8° C. was similar to that of the 3.75 mg LB/mL PG/G formulation stored at 25° C. When DEFINITY® was stored at 25° C., however, the level of total impurities dramatically increased.

These data demonstrate that the 3.75 mg LB/mL PG/G formulation is far more robust than the DEFINITY® formulation at higher temperatures. This observation was unexpected.

Example 4. Stability of Buffered Lipid Blend/Propylene Glycol/Glycerol Formulation New formulation lipid blend sample from Example 1, in 1:1 (v:v) propylene glycol/glycerol containing 0.005M acetate (75/25 sodium acetate/acetic acid), benzoate (75/25 sodium benzoate/benzoic acid) or salicylate (90/10 sodium salicylate/salicylic acid) buffer was filled into 2 cc Wheaton glass vial, the headspace replaced with PFP gas, a West, grey butyl lyo stopper, inserted and the vial crimped with an aluminum seal. Vials were stored at 25° C., prepared and analyzed as described in Example 2. Results for DEFINITY® analyzed as described in Example 2 are provided for comparison. Table 5 provides the total impurity as a percentage of the total lipid content in the vial at 25° C.

FIG. 3 illustrates the total impurity levels as a function of time. When DEFINITY® was stored at 25° C., however, the level of total impurities dramatically increased. These data demonstrate that the 3.75 mg Buffered LB/mL PG/G formulation is far more robust than the DEFINITY® formulation at higher temperatures. This observation was unexpected.

TABLE 5

Impurity data for 3.75 mg Lipid Blend/mL Buffered PG/G formulation stored at 25° C.

|  | 3.75 mg Lipid Blend/mL Buffered* PG/G Formulation | | | DEFINITY® (0.75 mg Lipid Blend/mL) |
|---|---|---|---|---|
|  | 75/25 Acetate | 75/25 Benzoate | 90/10 Salicylate | |
| Number of days at 25° C. | 50 | 50 | 50 | 2 Months |
| Total Impurity | 0.562 | 0.658 | 1.475 | 8.94 |

*5 mM buffer in 391 mg of PG/G containing LB, (0.33 wt % LB; 44.9 wt % PG; 54.8 wt % G; ratio of 1:138:168 for LB:PG:G). Ratios represent sodium acetate to acetic acid, sodium benzoate to benzoic acid, sodium salicylate to salicylic acid.

Example 5. Stability of Lipid Blend Glycerol Formulation

New formulation lipid blend sample from Example 1 in glycerol was filled into 2 cc HPLC glass vial, the headspace replaced with PFP gas, and the vial sealed with a screw cap containing a septum. Vials were stored at 25° C. and prepared and analyzed as described in Example 2.

Results for DEFINITY® analyzed as described in Example 2 are provided for comparison. Table 6 provides the total impurity results for this experiment. These data demonstrate that the 7.5 mg buffered LB/mL G formulation is far more robust than the DEFINITY® formulation at higher temperatures. This observation was unexpected.

TABLE 6

Impurity data for 7.50 mg Lipid Blend/mL glycerol (G) formulation* stored at 25° C.

|  | 7.5 mg Lipid Blend/mL G | DEFINITY® (Lot 4519M) (0.75 mg Lipid Blend/mL) |
|---|---|---|
| Number of Days at 25° C. | 149 days (approximately 5 months) | 6 months |
| PERCENT TOTAL IMPURITY | 2.478 | 23.17 |

*215 mg of G containing LB, 0.59 wt % LB (ratio of 1:168 for LB:G).

Example 6. Stability of Lipid Blend Powder

LB powder was stored in an amber bottle with a PTFE lined cap at 25° C. Samples were prepared in a methanol (50%), propylene glycol (10%), glycerin (10%) ammonium acetate (30%, 5 mM) solution. The solution was transferred to a HPLC vial and analyzed using a gradient reverse phase HPLC with evaporative light scattering Detection, (ELSD) using a C18 column and mobile phase containing: water, methanol, ammonium acetate, and triethylamine.

Table 7 provides stability data for lipid blend powder compared to DEFINITY® stored at 25° C.

These data demonstrate that the lipid blend powder is far more robust than the DEFINITY® formulation at higher temperatures.

TABLE 7

Impurity Data for Lipid Blend Powder

|  | LB powder 25° C. | DEFINITY ® (0.75 mg Lipid Blend/mL) 25° C. |
|---|---|---|
| Number of Days at 25° C. | 87 days (approximately 3 months) | 3 months |
| PERCENT TOTAL IMPURITY | 1.747 | 11.86 |

Example 7. Activation of DEFINITY®

The commercially available, FDA approved, ultrasound contrast agent, DEFINITY® (Lantheus Medical Imaging, Inc.) is put into an active form ("activated") by mechanical shaking (described in U.S. Pat. No. 6,039,557, the content of which are hereby incorporated by reference and may be used in the present process) of the PFP/lipid solution using a VIALMIX®. This results in incorporation of gas into lipid microspheres and represents the active product (see DEFINITY® prescribing information). Optimal VIALMIX® activation of DEFINITY® consistently produces gas filled microspheres that can be analyzed for number and size distribution using a particle sizer (Malvern FPIA-3000 Sysmex) when diluted into an appropriate sheath solution (see Table 8) having lower and upper cutoffs of 1 and 40 microns.

TABLE 8

DEFINITY ® bubble number and size analyzed using a Malvern FPIA-3000 Sysmex.

| DEFINITY ® Sample | Microsphere Mean Diameter (microns)[a] | Micro sphere per mL (×10$^9$)[b] |
|---|---|---|
| Sample 1 | 1.7 | 2.67 |
| Sample 2 | 1.6 | 3.20 |
| Sample 3 | 1.7 | 3.20 |
| Sample 4 | 1.7 | 1.75 |
| Sample 5 | 1.6 | 2.77 |
| Sample 6 | 1.6 | 2.97 |
| Average | 1.7 | 2.76 |

[a]Mean microsphere diameter for microspheres ranging from 1 to 40 microns.
[b]Mean microsphere concentration for microspheres ranging from 1 to 40 microns.

Acoustic attenuation was measured for selected samples using a Philips Sonos 5500 clinical ultrasound imaging system. Samples were diluted 1:7.7 (1.3 ml plus 8.7 ml saline) in a 10 ml syringe. 200 microliter samples from this syringe were pipetted into a beaker containing 200 ml of 0.9% saline at room temperature. A 2 cm stirring bar maintained solution uniformity and the s3 transducer of the ultrasound system was positioned at the top of the beaker, just into the solution and 8.9 cm above the upper margin of the stirring bar. 5 seconds of 120 Hz images were then acquired digitally and written to disk. The US system was used in IBS mode, TGC was fixed at the minimal value for all depths, and LGC was disabled. The mechanical index (MI) was 0.2 with power set 18 dB below maximum. The receive gain was fixed at 90 and the compression at 0. For each sample tested US data acquisition was acquired prior to (blank) and after sample injection. Measurements were taken at 20, 60 and 120 seconds after introduction of the sample into the beaker.

Image analysis was performed using Philips QLab, which read files produced by the US system and calculated values in dB for IBS mode. Regions of interest were drawn on the stirring bar and the dB values averaged over the full 5 second (approximately 360 video frame) acquisition. Attenuation measurements were obtained by subtracting the sample ROI value from the blank ROI value (both in dB). This was divided by twice the distance between the US transducer and the upper margin of the stirring bar to yield attenuation in dB/cm. Final values were obtained by applying a linear regression of the samples taken with respect to time after introduction to the beaker. The values used were derived from the intercept of the regression line with the y-axis.

TABLE 9

DEFINITY ® acoustic attenuation measurement[a]

|  | Vial 1 | Vial 2 | Vial 3 | Mean | SD |
|---|---|---|---|---|---|
| DEFINITY ® | 2.06 | 1.97 | 2.30 | 2.11 | 0.17 |

[a]The acoustic attenuation of DEFINITY ® was determined using a Philips Sonos 5500.

Example 8. Activation of Non-Aqueous Formulations

New formulations of lipid blend described in Example 1 were weighed into 2 cc Wheaton glass vials, diluent added if required, the headspace replaced with PFP gas, a West, grey butyl lyo stopper, inserted and the vial crimped with an aluminum seal. Diluent was injected through the stopper if required, and the vial was mechanically shaken using VIALMIX® for a duration to produce optimum product activation. Microsphere number and distribution was determined and some activated formulations were examined for ultrasound attenuation by the methods described in Example 7.

TABLE 10

Microsphere characteristics for 7.5 mg lipid blend/mL PG formulation with formulation diluent[a] added just prior to activation.

| Sample | Microsphere Mean Diameter (microns) | Microsphere per mL (×10$^9$) |
|---|---|---|
| LB/PG formulation (add diluent then cap)[b] | 1.82 | 1.76 |
| LB/PG formulation (capped, then inject diluents through stopper )[c] | 1.82 | 1.92 |

[a]Formulation diluent contained glycerol, phosphate buffer and saline to match the DEFINITY ® vial composition upon dilution of formulation.
[b] 177 mg propylene glycol formulation (0.72 wt % LB; ratio of 1:138 for LB:PG), 1.59 mL diluent[a] added, the headspace replaced with PFP, the 2 mL vial sealed with a West grey butyl stopper, crimped with an aluminum seal, the vial activated for 45 sec with a VIALMIX ® and tested for microsphere number and average size as described in Example 7.
[c]177 mg propylene glycol formulation (0.72 wt % LB; ratio of 1:138 for LB:PG) in 2 mL vial, the headspace replaced with PFP and the vial capped and crimped. Diluent[a], 1.59 mL, was injected through the stopper into vial using a disposable syringe, the vial was immediately activated for 45 sec with a VIALMIX ® and then tested as described in Example 7.

TABLE 11

Microsphere characteristics and acoustic attenuation for 7.5 mg lipid blend/mL PG formulation with saline added just prior to activation.

| Sample | Microsphere Mean Diameter (microns) | Microsphere per mL (×10$^9$) | Mean (SD) Acoustic Attenuation$^b$ (dB/cm) |
|---|---|---|---|
| LB/PG formulation (add saline then cap)$^a$ | 1.84 | 1.88 | 2.13 (0.34) |

$^a$177 mg propylene glycol formulation (0.72 wt % LB; ratio of 1:138 for LB:PG), 1.59 mL 0.9% saline added, the headspace replaced with PFP, the 2 mL vial sealed with a West grey butyl stopper, crimped with an aluminum seal, the vial activated and tested for microsphere number and average size as described in Example 7.
$^b$Acoustic attenuation determined as described in Example 7.

TABLE 12

Microsphere characteristic and acoustic attenuation for 7.5 mg lipid blend/mL PG/G formulations

| Sample | Microsphere Mean Diameter (microns) | Microsphere per mL (×10$^9$) | Mean Acoustic (SD) Attenuation$^c$ (dB/cm) |
|---|---|---|---|
| LB/PG/G formulation with saline added followed by activation$^a$ | 1.68 | 2.65 × 10$^9$ | Not determined |
| LB/PG/G formulation, activated and then diluted with saline$^b$ | 1.82 | 2.23 × 10$^9$ | 2.12 (0.27) |

$^a$391 mg propylene glycol and glycerol formulation (0.33% LB; 44.9% PG; 54.8% G; ratio of 1:138:168 for LB:PG:G), 1.38 mL 0.9% saline added, the headspace replaced with PFP, the 2 mL vial sealed with a West grey butyl stopper, crimped with an aluminum seal, the vial activated and tested for microsphere number and average size as described in Example 7.
$^b$391 mg propylene glycol and glycerol formulation (0.33% LB; 44.9% PG; 54.8% G; ratio of 1:138:168 for LB:PG:G), the headspace replaced with PFP, and the vial capped and crimped as described in footnote a above. Saline, 1.38 mL, was injected into vial using a disposable syringe, the vial immediately activated and then tested as described in Example 7.
$^c$Acoustic attenuation determined as described in Example 7.

TABLE 13

Microsphere characteristics for 7.5 mg lipid blend/mL buffered (5 mM) PG/G formulations with saline diluent added after activation.

| Sodium Acetate to Acetic Acid Ratio (5 mM total acetate) | Microsphere Mean Diameter (microns) | Microsphere per mL (×10$^9$) |
|---|---|---|
| 90:10 | 1.72 | 3.37 × 10$^9$ |
| 80:20 | 1.70 | 4.69 × 10$^9$ |
| 70:30 | 1.74 | 3.83 × 10$^9$ |
| 50:50 | 1.71 | 3.67 × 10$^9$ |
| 10:90 | 1.82 | 3.01 × 10$^9$ |

$^a$391 mg buffered propylene glycol and glycerol formulation, (0.33% LB; 44.9% PG; 54.8% G; ratio of 1:138:168 for LB:PG:G), the 2 mL vial sealed with a West grey butyl stopper, crimped with an aluminum seal, the vial activated, 1.38 mL 0.9% saline added, the vial mixed and tested for microsphere number and average size as described in Example 7.

These studies demonstrate that lipid blend formulated in a) PG b) PG/G c) buffered PG/G can be activated to form microspheres that have equivelent characteristics and acoustic attenuation to activated DEFINITY® (as shown in Example 7) by simply adding diluent and shaking on a VIALMIX®. This demonstrates pre-formulation with aqueous diluent is not required and simple addition is sufficient. Furthermore the diluent can be added to the lipid formulation by injecting through the vial stopper. In addition the lipid blend in PG/G can be activated to form microspheres that have equivalent characteristics and acoustic attenuation to activated DEFINITY® (as shown in Example 7) by shaking before the diluent is added. These findings are surpising.

Example 9. Activation of Individual Lipids or Lipid Blend

A formulation (Individual Lipid Formulation) was prepared by mixing the individual phospholipids (DPPA, DPPC and MPEG5000 DPPE) in propylene glycol at 0.045:0.401:0.304 (w:w:w) ratio (the same as the ratio for lipid blend). The resulting 7.5 mg/mL Individual lipid propylene glycol formulation was added to diluent (containing glycerol, phosphate buffer and saline to match the DEFINITY® vial composition) and mixed to form a final total lipid concentration of 0.75 mg/mL. A 1.7 mL aliquot was added to a 2 cc Wheaton glass vial, the headspace replaced with PFP gas, a West, grey butyl lyo stopper, inserted and the vial crimped with an aluminum seal. The vial was activated with a VIALMIX® and analyzed using the Sysmex FPIA 3000 for microsphere number and mean microsphere size.

TABLE 14

Microsphere characteristics for 7.5 mg individual lipid/mL PG formulation

| | Microsphere Mean Diameter (microns) | Microsphere per mL (×10$^9$) |
|---|---|---|
| Individual Lipid Formulation | 1.7 | 2.46 |

This study demonstrates that mixing individual lipids in PG, without preparing a lipid blend, can produce a formulation that allows mixing with a diluent to form a solution that can be activated to produce microspheres with characteristics equivalent to activated DEFINITY® (when compared with Example 7).

In another experiment, lipid blend was weighed into a 2 cc Wheaton glass vial, matrix (PG/G/saline) was added to the vial, the headspace replaced with PFP gas, a West, grey butyl lyo stopper, inserted, the vial crimped with an aluminum seal and then activated at 25° C. with a VIALMIX® and analyzed using the Sysmex FPIA 3000 for microsphere number and mean microsphere size. The results are presented in Table 15.

TABLE 15

Microsphere characteristics for Lipid Blend Powder (1.275 mg) in a vial with PFP headspace

| | Microsphere Mean Diameter (microns) | Microsphere per mL (×10$^9$) |
|---|---|---|
| Lipid Blend Formulation | 1.63 | 4.10 |

This study demonstrates that lipid blend powder could be weighed into a vial, diluent added, headspace replaced with PFP, and the vial activated to produce microspheres with characteristics equivalent to activated DEFINITY® (when compared with Example 7). This demonstrates the lipids did not need to be pre-formulated to allow activation.

Example 10. Activation of Different Lipid Concentrations

Lipid blend, as described in Example 1, was used to make formulations at varying total lipid blend concentrations by mixing different amounts of LB powder in either propylene glycol (PG) or 1:1 v/v propylene glycol/glycerol (PG/G). Each lipid formulation was weighed into 2 cc Wheaton glass vials, diluent added if required, the headspace replaced with PFP gas, a West, grey butyl lyo stopper, inserted and the vial crimped with an aluminum seal. The vials were mechanically shaken using VIALMIX® to activate the product and diluent added, if needed, through the stopper using a syringed equipped with a needle. Microsphere number and distribution were determined as described in Example 7.

TABLE 16

Microsphere characteristics with different lipid mg/mL PG formulations[a]

| Lipid Blend concentration in formulation | Time of Dilution | Lipid Blend concentration after dilution | Microsphere per mL (×10$^9$) | Diameter (μm) |
|---|---|---|---|---|
| DEFINITY ® 0.75 mg Lipid Blend per mL[d] | n/a | n/a | 3.05 | 1.66 |
| 7.5 mg Lipid Blend/mL PG | Before Activation[b] | 0.75 mg/mL | 4.55 | 1.63 |
| 7.5 mg Lipid Blend/mL PG | Before Activation[c] | 0.75 mg/mL | 4.65 | 1.72 |
| DEFINITY ® diluted to 0.375 mg Lipid Blend per mL[d] | Before activation | 0.375 mg/mL | 1.38 | 1.66 |
| 3.75 mg Lipid Blend/mL PG | Before Activation[b] | 0.375 mg/mL | 2.24 | 1.7 |
| 3.75 mg Lipid Blend/mL PG | Before Activation[c] | 0.375 mg/mL | 2.69 | 1.72 |
| DEFINITY ® diluted to 0.1875 mg Lipid Blend per mL[d] | Before activation | 0.1875 mg/mL | 0.54 | 1.75 |
| 1.875 mg Lipid Blend/mL PG | Before Activation[b] | 0.1875 mg/mL | 0.892 | 1.72 |
| 1.875 mg Lipid Blend/mL PG | Before Activation[c] | 0.1875 mg/mL | 1.25 | 1.74 |

[a]Vials (2 cc Wheaton vials) were prepared by weighting 177 mg of propylene glycol containing 1.875, 3.75 or 7.5 mg lipid blend/mL (ratios of 1:552; 1:276; and 1:138 for LB:PG, respectively).
[b]Vials were diluted with 8:1 (v:v) saline and glycerol to a final volume of 1.7 mL just prior to activation. The air headspace was then exchanged with PFP, sealed with a West grey butyl stopper, the vial crimped with an aluminum seal, activated and tested for microsphere number and average size as described in Example 7.
[c]Vials were diluted with saline to a final volume of 1.7 mL just prior to activation. The air headspace was then exchanged with PFP, sealed with a West grey butyl stopper, the vial crimped with an aluminum seal, activated and tested for microsphere number and average size as described in Example 7.
[d]Vials (2 cc Wheaton vials) were prepared by diluting DEFINITY ® with formulation matrix 1 to 4 or 1 to 2 (undiluted DEFINITY ® was also tested), the headspace gas exchanged with PFP, the vials stoppered and crimped with an aluminum seal, activated and tested for microsphere number and average size as described in Example 7.

TABLE 17

Microsphere characteristics with different Lipid mg/mL PG/G formulations[a]

| Lipid Blend concentration in formulation | Time of Dilution | Lipid Blend concentration after dilution, | Microsphere per mL (×10$^9$) | Diameter (μm) |
|---|---|---|---|---|
| DEFINITY ® 0.75 mg Lipid Blend per mL[d] | n/a | n/a | 3.05 | 1.66 |
| 3.75 mg Lipid Blend/mL PG/G | Before Activation[b] | 0.75 mg/mL | 4.71 | 1.66 |
| 3.75 mg Lipid Blend/mL PG/G | After Activation[c] | 0.75 mg/mL | 3.12 | 1.60 |
| DEFINITY ® diluted to 0.375 mg Lipid Blend per mL[d] | Before activation | 0.375 mg/mL | 1.38 | 1.66 |
| 1.875 mg Lipid Blend/mL PG/G | Before Activation[b] | 0.375 mg/mL | 2.45 | 1.74 |
| 1.875 mg Lipid Blend/mL PG/G | After Activation[c] | 0.375 mg/mL | 1.73 | 1.66 |
| DEFINITY ® diluted to 0.1875 mg Lipid Blend per mL[d] | before activation | 0.1875 mg/mL | 0.54 | 1.75 |

TABLE 17-continued

Microsphere characteristics with different Lipid mg/mL PG/G formulations[a]

| Lipid Blend concentration in formulation | Time of Dilution | Lipid Blend concentration after dilution, | Microsphere per mL ($\times 10^9$) | Diameter (μm) |
|---|---|---|---|---|
| 0.9375 mg Lipid Blend/mL PG/G | Before Activation[b] | 0.1875 mg/mL | 1.00 | 1.72 |
| 0.9375 mg Lipid Blend/mL PG/G | After Activation[c] | 0.1875 mg/mL | 0.41 | 1.89 |

[a] Vials (2 cc Wheaton vials) were prepared by weighting 391 mg of 1:1 (v/v) propylene glycol and glycerol containing 0.9375, 1.875 or 3.75 mg lipid blend/mL (ratios of 1:552:672; 1:276:336; and 1:138:168 for LB:PG:G, respectively).
[b] Vials were diluted with saline to a final volume of 1.7 mL just prior to activation. The air headspace was then exchanged with PFP, sealed with a West grey butyl stopper, the vial crimped with an aluminum seal, activated and tested for microsphere number and average size as described in Example 7.
[c] The air headspace was exchanged with PFP, the vial sealed with a West grey butyl stopper, crimped with an aluminum seal and activated. Saline was added to a final volume of 1.7 mL and the vial tested for microsphere number and average size as described in Example 7.
[d] Vials (2 cc Wheaton vials) were prepared by diluting DEFINITY ® with formulation matrix 1 to 4 or 1 to 2 (undiluted DEFINITY ® was also tested), the headspace gas exchanged with PFP, the vials stoppered and crimped with an aluminum seal, activated and tested for microsphere number and average size as described in Example 7.

These studies demonstrated that lipid blend formulations having different lipid concentrations, when activated, produce proportional numbers of microspheres (per given volume, 1 mL). The microsphere size was equivalent to activated DEFINITY® and microsphere number similar or higher than activated DEFINITY® or an equivalent diluted form. The ability to form microspheres with characteristics equivalent to activated DEFINITY® with a variety of different lipid blend concentrations in PG or PG/G was not expected. The ability to achieve this by activating lipid blend in PG/G before the addition of diluents was even further surprising.

Example 11. Containers

New lipid formulations or DEFINITY® were filled into various containers including: vials, syringes, and pliable plastic tubes, which were then activated. In all studies, an appropriate amount of lipid formulation was placed in the container, the headspace replaced with PFP, the container sealed, and the formulation activated.

TABLE 18

Microsphere characteristics for lipid blend in PG or PG/G formulations activated in 2 mL Schott vial[a]

| Fill Weight | Time of Dilution | Volume of Saline Dilution (mL) | Microsphere Mean Diameter (microns) | Microsphere per mL ($\times 10^9$) |
|---|---|---|---|---|
| 55 mg of 7.5 mg LB/mL of PG | Before Activation | 0.50 | 1.52 | 6.23 |
| 89 mg of 7.5 mg LB/mL of PG | Before Activation | 0.80 | 1.52 | 4.83 |
| 134 mg of 7.5 mg LB/mL of PG | Before Activation | 1.20 | 1.61 | 5.29 |
| 177 mg of 7.5 mg LB/mL of PG | Before Activation | 1.59 | 1.63 | 5.00 |
| 122 mg of 3.75 mg LB/mL of PG/G | Before Activation | 0.43 | 1.57 | 5.43 |
| 196 mg of 3.75 mg LB/mL of PG/G | Before Activation | 0.69 | 1.55 | 5.31 |
| 295 mg of 3.75 mg LB/mL of PG/G | Before Activation | 1.04 | 1.61 | 4.48 |
| 392 mg of 3.75 mg LB/mL of PG/G | Before Activation | 1.38 | 1.60 | 4.96 |
| 196 mg of 3.75 mg LB/mL of PG/G | After Activation | 0.69 | 1.88 | 1.77 |
| 295 mg of 3.75 mg LB/mL of PG/G | After Activation | 1.04 | 1.69 | 2.68 |
| 392 mg of 3.75 mg LB/mL of PG/G | After Activation | 1.38 | 1.56 | 4.06 |

[a] The appropriate amount of 7.5 mg LB/mL PG or 3.75 mg LB per mL PG/G formulation was weighed into a 2 mL Schott vial, an appropriate amount of saline added for "before activation" samples, the air headspace replaced with PFP, the vial sealed with West grey butyl stoppers, crimped with an aluminum seal, activated, an appropriate amount of saline added for "after activation samples", and tested for microsphere number and average size as described in Example 7. Vials were activated using a VIALMIX ®.

TABLE 19

Microsphere characteristics for lipid blend in PG or PG/G formulations activated in 1 mL Wheaton V-vial[a]

| Fill Weight | Time of Dilution | Volume of Saline Dilution (mL) | Microsphere Mean Diameter (microns) | Microsphere per mL ($\times 10^9$) |
|---|---|---|---|---|
| 55 mg of 7.5 mg LB/mL of PG | Before Activation | 0.50 | 1.64 | 6.33 |
| 88 mg of 7.5 mg LB/mL of PG | Before Activation | 0.80 | 1.73 | 4.04 |
| 177 mg of 7.5 mg LB/mL of PG | Before Activation | 1.59 | 1.63 | 5.00 |
| 122 mg of 3.75 mg LB/mL of PG/G | Before Activation | 0.43 | 1.57 | 5.28 |
| 392 mg of 3.75 mg LB/mL of PG/G | Before Activation | 1.38 | 1.60 | 4.96 |
| 122 mg of 3.75 mg LB/mL of PG/G | After Activation | 0.43 | 1.78 | 1.06 |
| 392 mg of 3.75 mg LB/mL of PG/G | After Activation | 1.38 | 1.68 | 3.07 |

[a] The appropriate amount of 7.5 mg LB/mL PG or 3.75 mg LB/mL PG/G formulation was weighed into a 1 mL Wheaton V-vial, the air headspace replaced with PFP, an appropriate amount of saline added for "before activation" samples, the vial sealed with West grey butyl stoppers, crimped with an aluminum seal, activated, an appropriate amount of saline added for "after activation" samples, and tested for microsphere number and average size as described in Example 7. Vials were activated using a VIALMIX ®.

TABLE 20

Microsphere concentration for DEFINITY ® activated in syringes[a]

| Syringe Size | Volume (mL) of DEFINITY ® | Microsphere Mean Diameter (microns) | Microsphere per mL (×10$^9$) |
|---|---|---|---|
| 3 mL | 1.5 | 1.63 | 2.45 |
| 5 mL | 1.6 | 1.78 | 0.961 |
| 5 mL | 1.9 | 1.92 | 1.00 |
| 5 mL | 2.25 | 1.76 | 2.25 |
| 5 mL | 2.7 | 1.78 | 0.513 |

[a]DEFINITY ® filled (1.5 to 2.7 mL) into 3 and 5 mL NORM-JECT ® syringes ((Henke-Sass, Wolf GmbH, Tuttlingen, Germany)), The air headspace was replaced with PFP, the syringe activated with a Wig-L-Bug ™, tested for microsphere number and average size as described in Example 7.

TABLE 21

Microsphere characteristics for lipid blend in PG or PG/G formulations activated in 3 mL NORM-JECT ® syringe

| Fill Weight | Time of Dilution | Volume of Saline Dilution (mL) | Microsphere Mean Diameter (microns) | Microsphere per mL (×10$^9$) |
|---|---|---|---|---|
| 101 mg of 7.5 mg LB/mL of PG | Before Activation | 0.90 | 1.79 | 4.02 |
| 177 mg of 7.5 mg LB/mL of PG | Before Activation | 1.59 | 1.66 | 4.15 |
| 222 mg of 7.5 mg LB/mL of PG | Before Activation | 0.78 | 1.72 | 3.63 |
| 222 mg of 3.75 mg LB/mL of PG/G | After Activation | 0.78 | 1.57 | 4.83 |

[a]The appropriate amount of 7.5 mg LB/mL PG or 3.75 mg LB/mL PG/G formulation was weighed into a 3 mL NORM-JECT ® syringe ((Henke-Sass, Wolf GmbH, Tuttlingen, Germany), an appropriate amount of saline added for "before activation" samples, the air headspace replaced with PFP and the syringe activated, an appropriate amount of saline added for "after activation" samples, and the preparations tested for microsphere number and average size as described in Example 7. Syringes were activated using a VIALMIX ®.

TABLE 22

Microsphere characteristics for lipid blend in PG Formulations activated in syringe modified to have two compartments formed with a dental amalgam capsule[a]

| Fill Weight[b] | Time of Dilution | Volume of Saline Dilution (mL) | Microsphere Mean Diameter (microns) | Microsphere per mL (×10$^9$) |
|---|---|---|---|---|
| 177 mg of 7.5 mg LB/mL of PG | Before Activation | 1.59 | 1.66 | 4.15 |
| 391 mg of 3.75 mg LB/mL of PG/G | Before Activation | 1.38 | 1.64 | 4.14 |
| 391 mg of 3.75 mg LB/mL of PG/G | After Activation | 1.38 | 1.59 | 3.92 |

[a]A 5 mL NORM-JECT ® syringe (Henke-Sass, Wolf GmbH, Tuttlingen, Germany) was cut down to 3 mL. A dental amalgam capsule (obtained from a local dentist) was opened, the bottom containing powder was removed, and the plunger was removed from the top compartment along with the contents of the top compartment. The top compartment was fitted into the barrel of the cut down syringe.
[b]The appropriate amount of 7.5 mg LB/mL PG or 3.75 mg LB/mL PG/G formulation was weighed into the body of a 5 mL NORM-JECT ® syringe cut down to approximately 2.5 mL ((Henke-Sass, Wolf GmbH, Tuttlingen, Germany), the dental amalgam plunger was inserted into the capsule, an appropriate amount of saline added for "before activation" samples, the air headspace replaced with PFP, the syringe sealed with a luer lock cap, activated, an appropriate amount of saline added for "after activation" samples, and tested for microsphere number and average size as described in Example 7. Vials were activated using a VIALMIX ®.

TABLE 23

Microsphere characteristics for lipid blend in PG or PG/G formulations activated in syringe modified to have two compartments[a]

| Fill Weight[b] | Time of Dilution | Volume of Saline Dilution (mL) | Microsphere Mean Diameter (microns) | Microsphere per mL (×10$^9$) |
|---|---|---|---|---|
| 60 mg of 7.5 mg LB/mL of PG | Before Activation | 0.54 | 1.83 | 4.74 |
| 133 mg of 3.75 mg LB/mL of PG/G | Before Activation | 0.47 | 1.72 | 4.42 |
| 133 mg of 3.75 mg LB/mL of PG/G | After Activation | 0.47 | 1.89 | 1.40 |

[a]A 3 mL NORM-JECT ® syringe (Henke-Sass, Wolf GmbH, Tuttlingen, Germany) was modified to have an approximate 3 mm by 10 mm × 1 mm bulge as a bypass channel typical of commercial two compartment syringes. The channel was made by heating one tong of a forceps and pressing it to the inside of the syringe barrel at about the 2 mL volume mark. The end of a syringe plunger was cut off to a length of approximately 1 cm and used as the bypass plug. A second syringe plunger was also cut down.
[b]The appropriate amount of 7.5 mg LB/mL PG or 3.75 mg LB/mL PG/G formulation was weighed into the body of the modified 3 mL NORM-JECT ® syringe below the bypass channel, the bypass plug was inserted to a point just above the bypass channel, an appropriate amount of saline was added to the top chamber formed after insertion of the bypass plug, the cutdown syringe plunger was inserted completing the fill of the upper chamber. The air headspace in the lower chamber was replaced with PFP, the syringe sealed with a luer lock cap. The syringe was activated using a VIALMIX ®, the syringe plunger pushed to move the bypass plug to the bypass channel, allowing the saline to enter the lower chamber containing activated product for the "after activation" samples. For the "before activation" samples, the syringe plunger was pushed to move the bypass plug to the bypass channel, allowing the saline to enter the lower chamber the syringe activated using a VIALMIX ®. Samples were tested for microsphere number and average size as described in Example 7.

TABLE 24

Microsphere characteristics for lipid blend PG or PG/G formulations activated in two compartment plastic tube

| Fill Weight[a] | Time of Dilution | Volume of Saline Dilution (mL) | Microsphere Mean Diameter (microns) | Microsphere per mL (×10$^9$) |
|---|---|---|---|---|
| 177 mg of 7.5 mg LB/mL of PG | Before Activation | 1.59 | 1.64 | 3.11 |
| 392 mg of 3.75 mg LB/mL of PG/G | Before Activation | 1.38 | 1.80 | 2.62 |
| 392 mg of 3.75 mg LB/mL of PG/G | After Activation | 1.38 | 1.63 | 3.72 |

[a]The appropriate amount of 7.5 mg LB/mL PG or 3.75 mg LB/mL PG 7 G formulation was weighed into the lower chamber of a two compartment tube (NEOPAC Fleximed Tube, 13.5 × 80 mm, Hoffmann Neopac AG, Oberdiessbach, Switzerland), an appropriate amount of saline was added to the top chambert, the air headspace in the lower chamber was replaced with PFP, the tube sealed with a luer lock cap. The tube was activated using a VIALMIX ®, the upper compartmet saline was transferred to the lower compartment and mixed, for the "after activation" samples. For the 'before activation" samples, the saline was tranferred to the lower compartment before the tube activation using a VIALMIX ®. Samples were tested for microsphere number and average size as described in Example 7.

These studies demonstrated that the process of shaking lipid blend PG and PG/G formulations with a mechanical shaker could be achieved in a variety of containers including vials, syringes and a plastic tube and produce microspheres with characteristics equivalent to activated DEFINITY®. Surprisingly, the mechanical shaking overcame differences in the dimensions of the container and the material the container was made from and allowed the formation of microspheres with equivalent size and number to be formed. Activation of the LB formulations in PG and PG/G in syringes both before and after addition of diluents is an exciting finding. In addition being able to separate the diluents from the formulation and then allow the two components to come together prior to or after activation by mechanical shaking proves new opportunities to provide preparations that can achieve a room temperature stable formulation with an easy product production.

Example 12. Activation Methods

Studies were conducted to demonstrate the ability to activate DEFINITY® with several methods other than use of the VIALMIX®. These methods are described below with results reported in Table 25.

A. DEFINITY® (1.5 mL) was drawn into a 3 ml plastic syringe and connected to a 3 way stopcock. A separate syringe of the same size was filled with PFP gas and connected to another port on the stopcock. The DEFINITY® and PFP gas were mixed by alternately depressing the plunger on each syringe back and forth between 50-400 times. Microbubble count and bubble diameter measurements indicate activation of DEFINITY®.

B. DEFINITY® (3.0 mL) was drawn into a 10 ml plastic syringe and connected to a 3 way stopcock. A separate syringe of the same size was filled with PFP gas and connected to another port on the stopcock. The DEFINITY® and PFP gas were mixed by alternately depressing the plunger on each syringe back and forth 200 times. Microbubble count and bubble diameter measurements indicate activation of DEFINITY®.

C. A lipid formulation (1.5 mL of 0.045 mg/mL DPPA, 0.75 mg/mL DPPC, 0 mg/mL MPEG5000DPPE, 4.87 mg NaCl/mL, 103.5 mg/mL propylene glycol, 126.2 mg/mL glycerol, 2.34 mg/mL $NaH_2PO_4H_2O$, 2.16 mg/mL $NaHPO_47H_2O$) was drawn into a 3 ml plastic syringe and connected to a 3 way stopcock. A separate syringe of the same size was filled with PFP gas and connected to another port on the stopcock. The formulation and PFP gas were mixed by alternately depressing the plunger on each syringe back and forth 100 times. Microbubble count and bubble diameter measurements indicate activation of this lipid formulation.

D. A modified lipid formulation (1.5 mL of 0.045 mg/mL DPPA, 0.75 mg/mL DPPC, 0 mg/mL MPEG5000DPPE, 4.87 mg/mL NaCl, 103.5 mg/mL propylene glycol, 126.2 mg/mL glycerol, 2.34 mg/mL $NaH_2PO_4H_2O$, 2.16 mg/mL $NaHPO_47H_2O$) was drawn into a 3 ml plastic syringe and connected to a 3 way stopcock. A separate syringe of the same size was filled with PFP gas and connected to another port on the stopcock. In between the lipid formulation filled syringe and the stopcock was a plastic tube filed with seven high performance X-grid static mixers (StaMixCo, GXP-9, 4-PA66, black). The formulation and PFP gas were mixed by alternately depressing the plunger on each syringe back and forth 50 times. Microbubble count and bubble diameter measurements indicate activation of this lipid formulation.

E. A modified lipid formulation (1.5 mL of 0.045 mg/mL DPPA, 0.75 mg/mL DPPC, 0 mg/mL MPEG5000DPPE, 4.87 mg/mL NaCl, 103.5 mg/mL propylene glycol, 126.2 mg/mL glycerol, 2.34 mg/mL $NaH_2PO_4H_2O$, 2.16 mg/mL $NaHPO_47H_2O$) was drawn into a 3 ml plastic syringe and connected to two 3 way stopcocks in series. A separate syringe of the same size was filled with PFP gas and connected to another port on the stopcock. The formulation and PFP gas were mixed by alternately depressing the plunger on each syringe back and forth 100 times. Microbubble count and bubble diameter measurements indicate activation of this lipid formulation.

F. A modified lipid formulation (1.5 mL of 0.045 mg/mL DPPA, 0.75 mg/mL DPPC, 0 mg/mL MPEG5000DPPE, 4.87 mg/mL NaCl, 103.5 mg/mL propylene glycol, 126.2 mg/mL glycerol, 2.34 mg/mL $NaH_2PO_4H_2O$, 2.16 mg/mL $NaHPO_47H_2O$) was drawn into a 3 ml plastic syringe and connected to a 3 way stopcock. A separate syringe of the same size was filled with PFP gas and connected to another port on the stopcock. In between the lipid formulation filled syringe and the stopcock was a plastic tube filed with eight high performance X-grid static mixers (StaMixCo, GXF-10-2-ME, orange). The formulation and PFP gas were mixed by alternately depressing the plunger on each syringe back and forth 100 times. Microbubble count and bubble diameter measurements indicate activation of this lipid formulation.

G. A modified lipid formulation (1.5 mL of 0.045 mg/mL DPPA, 0.401 mg/mL DPPC, 0.304 mg/mL MPEG5000DPPE, 4.87 mg/mL NaCl, 155.25 mg/mL propylene glycol, 31.55 mg/mL glycerol, 2.34 mg/mL $NaH_2PO_4H_2O$, 2.16 mg/mL $NaHPO_47H_2O$) was drawn into a 3 ml plastic syringe and connected to a 3 way stopcock. A separate syringe of the same size was filled with PFP gas and connected to another port on the stopcock. The formulation and PFP gas were mixed by alternately depressing the plunger on each syringe back and forth 100 times. Microbubble count and bubble diameter measurements indicate activation of this lipid formulation.

H. DEFINITY® (1.5 mL) plus 3.5 mL of saline were drawn into a 5 ml plastic syringe and connected to a 3 way stopcock. A separate syringe of the same size was filled with PFP gas and connected to another port on the stopcock. The DEFINITY®, saline and PFP gas were mixed by alternately depressing the plunger on each syringe back and forth 100 times. Microbubble count and bubble diameter measurements indicate activation of DEFINITY®.

I. DEFINITY® (1.5 mL) was drawn into a 3 ml plastic syringe and connected to a 3 way stopcock. A separate syringe of the same size was filled with PFP gas and connected to another port on the stopcock. In between the DEFINITY® filled syringe and the stopcock was a plastic tube with a plastic helical mixer (StaMixCo, 2.5"×3/16", 15 helical turns in 2.5 inches). The DEFINITY® and PFP gas were mixed by alternately depressing the plunger on each syringe back and forth 50 times. Microbubble count and bubble diameter measurements indicate activation of DEFINITY®.

J. DEFINITY® (3.0 mL) was drawn into a 10 ml plastic syringe and connected to a 3 way stopcock. A separate syringe of the same size was filled with PFP gas and connected to another port on the stopcock. In between the DEFINITY® filled syringe and the stopcock was a plastic tube with a plastic helical mixer (StaMixCo, 2.5"×3/16", 15 helical turns in 2.5 inches). The DEFINITY® and PFP gas were mixed by alternately depressing the plunger on each syringe back and forth 50 times. Microbubble count and bubble diameter measurements indicate activation of DEFINITY®.

K. DEFINITY® (1.5 mL) was drawn into a 3 ml plastic syringe and connected directly to a plastic tube with a plastic helical mixer (StaMixCo, 2.5"×3/16", 15 helical turns in 2.5 inches). A separate syringe of the same size was filled with PFP gas and connected to the other end of the plastic tube. The DEFINITY® and PFP gas were mixed by alternately depressing the plunger on each syringe back and forth 25 times. Microbubble count and bubble diameter measurements indicate activation of DEFINITY®.

L. DEFINITY® (1.5 mL) was drawn into a 3 ml plastic syringe and connected directly to a 20 u QMA filter (Waters). A separate syringe of the same size was filled with PFP gas and connected to the other end of the filter. The DEFINITY® and PFP gas were mixed by alternately depressing the plunger on each syringe back and forth 50 times. Microbubble count and bubble diameter measurements indicate activation of DEFINITY®.

M. DEFINITY® (1.5 mL) was drawn into a 3 ml plastic syringe and connected directly to a 20 u QMA filter (Waters) and plastic tube with a plastic helical mixer (StaMixCo, 2.5"×3/16", 15 helical turns in 2.5 inches). A separate syringe of the same size was filled with PFP gas and connected to the other end of the mixer. The DEFINITY® and PFP gas were mixed by alternately depressing the plunger on each syringe back and forth 50 times. Microbubble count and bubble diameter measurements indicate activation of DEFINITY®.

N. DEFINITY® (0.6 mL) was drawn into a 1 ml glass syringe and connected to a 1.5 inch metal holder containing a 5 u filter. A separate glass syringe of the same size was filled with PFP gas and connected to the other end of the metal holder. This extrusion device is commercial available (LiposoFast-Basic, Avestin, Inc.) The DEFINITY® and PFP gas were mixed by alternately depressing the plunger on each syringe back and forth 25 times. Microbubble count and bubble diameter measurements indicate activation of DEFINITY®.

O. DEFINITY® (0.6 mL) was drawn into a 1 ml glass syringe and connected to a 1.5 inch metal holder containing a 5 u filter. A separate glass syringe of the same size was filled with PFP gas and connected to the other end of the metal holder. This extrusion device is commercial available (LiposoFast-Basic, Avestin, Inc.) The DEFINITY® and PFP gas were mixed by alternately depressing the plunger on each syringe back and forth 100 times. Microbubble count and bubble diameter measurements indicate activation of DEFINITY®.

P. DEFINITY® (0.6 mL) was drawn into a 1 ml glass syringe and connected to a 1.5 inch metal holder containing either a 0.4 or 1.0 micron filter. A separate glass syringe of the same size was filled with PFP gas and connected to the other end of the metal holder. This extrusion device is commercial available (LiposoFast-Basic, Avestin, Inc.) The DEFINITY® and PFP gas were mixed by alternately depressing the plunger on each syringe back and forth 25 times. Microbubble count and bubble diameter measurements indicate activation of DEFINITY®.

Q. A vial of DEFINITY® (1.5 mL) was vortexed at the highest setting for 5 minutes. Microbubble count and bubble diameter measurements indicate activation of DEFINITY®.

R. A vial of DEFINITY® (1.5 mL) was sonicated for 2 minutes. The solution was a milky white, however was not tested for microbubble count or bubble diameter measurements.

S. A vial of DEFINITY® (1.5 mL) was treated for 5 minutes with a high speed blade homogenizer. The solution was a milky white, however was not tested for microbubble count or bubble diameter measurements.

T. A vial of DEFINITY® (1.5 mL) was secured on the end of a 0.75"×2.25"×23" wood stick, moved between two wood posts 15" apart between 300 and 1500 times at rate of 100 hits/27 seconds, and tested for microbubble count or bubble diameter measurements. Microbubble count and bubble diameter measurements indicate activation of DEFINITY®.

TABLE 25

Results of microbubble counts and diameter using a Sysmex microbubble analyzer.

| Example | # of syringe barrel depressions back and forth (Example "T" is # hits) | # Microbubbles ($\times 10^9$) per ml | Microbubble Diameter (microns) |
|---|---|---|---|
| A | 50 | 0.80, 1.49 | 1.8-2.0 |
|   | 75 | 1.19 | 1.7 |
|   | 100 | 0.57, 1.25, 1.40 | 1.8, 1.9 |
|   | 200 | 1.28 | 1.7 |
|   | 400 | 1.02 | 1.6 |
| B | 200 | 0.55 | 1.7 |
| C | 100 | 1.28 | 1.7 |
| D | 50 | 0.50 | 1.9 |
| E | 100 | 0.99 | 1.7 |
| F | 100 | 0.69 | 2.0 |
| G | 100 | 1.08 | 2.0 |
| H | 100 | 0.08 | 2.3 |
| I | 50 | 0.23 | 1.9 |
| J | 50 | 0.16 | 1.9 |
| K | 25 | 0.14 | 2.0 |
| L | 50 | 0.07 | 2.1 |
| M | 50 | 0.11 | 2.1 |
| N | 25 | 0.10 | 1.7 |
| O | 100 | 0.57 | 1.3 |
| P | 0.4u and 1.0u filter 25 | 0.01 and 0.12 | 3.6 and 1.9 |
| Q | Vortex 5 min | 0.13 | 2.1 |
| R | Sonicate 2 min | Not tested based on visual-Light Milky | Not tested based on visual-Light Milky |
| S | Polytron 5 min | Not tested based on visual-Light Milky | Not tested based on visual-Light Milky |
| T | Between 300 and 1500 times at rate of 100 hits/27 seconds | | |
|   | 300x | 0.056 | 1.86 |
|   | 500x | 0.096 | 1.93 |
|   | 1000x | 0.205 | 1.90 |
|   | 1500x | 0.194 | 1.74 |

These studies demonstrate activation of DEFINITY® or modified versions thereof can be accomplished using a variety of activation devices.

The references recited herein, including patents and patent applications, are incorporated by reference in their entirety.

The invention claimed is:

1. A method of using lipid-encapsulated perfluoropropane gas microspheres for ultrasound contrast imaging comprising
    (1) forming lipid-encapsulated perfluoropropane gas microspheres by
        (a) forming a combined mixture by adding an aqueous diluent to a composition comprising a non-aqueous mixture in contact with a perfluoropropane gas, said non-aqueous mixture having less than 5% w/w (weight/weight) of water, and comprising DPPA, DPPC and MPEG-5000-DPPE in a ratio of about 10:82:8 (mole %), in propylene glycol and/or glycerol, and
        (b) activating the combined mixture to form lipid-encapsulated perfluoropropane gas microspheres, (2) administering the lipid-encapsulated perfluoropropane gas microspheres to a subject, and (3) obtaining an ultrasound image of the subject.

2. The method of claim 1, wherein the non-aqueous mixture has a lipid concentration of about 0.1 to about 10 mg per ml.

3. The method of claim 1, wherein the non-aqueous mixture consists essentially of DPPA, DPPC, MPEG5000-DPPE, propylene glycol, and glycerol.

4. The method of claim 3, wherein the weight ratio of DPPA, DPPC and MPEG5000-DPPE combined to propylene glycol to glycerol is in a range of about 1:100:100 to about 1:600:700.

5. The method of claim 1, wherein the lipid-encapsulated perfluoropropane gas microspheres have an average diameter ranging from about 1.0 microns to about 2.0 microns.

6. The method of claim 5, wherein the lipid-encapsulated perfluoropropane gas microspheres are present at a concentration of greater than $10^8$/mL after activation.

7. The method of claim 1, wherein the lipid-encapsulated perfluoropropane gas microspheres are present at a concentration of greater than $10^8$/mL after activation.

8. The method of claim 1, wherein activating the combined mixture comprises agitating the combined mixture for 20-45 seconds.

9. The method of claim 1, wherein the non-aqueous mixture consists essentially of DPPA, DPPC, MPEG5000-DPPE, and propylene glycol.

10. The method of claim 9, wherein the weight ratio of DPPA, DPPC and MPEG5000-DPPE, combined, to propylene glycol is in a range of about 1:100 to about 1:600.

11. A method of using lipid-encapsulated perfluoropropane gas microspheres for ultrasound contrast imaging comprising (1) forming lipid-encapsulated perfluoropropane gas microspheres by activating a composition comprising a non-aqueous mixture in contact with a perfluoropropane gas, said non-aqueous mixture having less than 5% w/w (weight/weight) water, and comprising DPPA, DPPC and MPEG5000-DPPE in a ratio of about 10:82:8 (mole %) in propylene glycol and/or glycerol, (2) administering the lipid-encapsulated perfluoropropane gas microspheres to a subject, and (3) obtaining an ultrasound image of the subject.

12. The method of claim 11, wherein the non-aqueous mixture has a lipid concentration of about 0.1 to about 10 mg per ml.

13. The method of claim 12, wherein an aqueous diluent is added to the lipid-encapsulated perfluoropropane gas microspheres prior to step (2).

14. The method of claim 11, wherein the non-aqueous mixture consists essentially of DPPA, DPPC, MPEG5000-DPPE, propylene glycol, and glycerol.

15. The method of claim 14, wherein an aqueous diluent is added to the lipid-encapsulated perfluoropropane gas microspheres prior to step (2).

16. The method of claim 11, wherein the lipid-encapsulated perfluoropropane gas microspheres have an average diameter ranging from about 1.0 microns to about 2.0 microns.

17. The method of claim 16, wherein the lipid-encapsulated perfluoropropane gas microspheres are present at a concentration of greater than $10^8$/mL after activation.

18. The method of claim 17, wherein an aqueous diluent is added to the lipid-encapsulated perfluoropropane gas microspheres prior to step (2).

19. The method of claim 16, wherein an aqueous diluent is added to the lipid-encapsulated perfluoropropane gas microspheres prior to step (2).

20. The method of claim 11, wherein the lipid-encapsulated perfluoropropane gas microspheres are present at a concentration of greater than $10^8$/mL after activation.

21. The method of claim 20, wherein an aqueous diluent is added to the lipid-encapsulated perfluoropropane gas microspheres prior to step (2).

22. The method of claim 11, wherein an aqueous diluent is added to the lipid-encapsulated perfluoropropane gas microspheres prior to step (2).

* * * * *